US011253567B2

(12) United States Patent
Horiba

(10) Patent No.: US 11,253,567 B2
(45) Date of Patent: Feb. 22, 2022

(54) CITRUS SEED EXTRACT-CONTAINING COMPOSITION, FOOD, DRUG, AND METHOD FOR PRODUCING CITRUS SEED EXTRACT-CONTAINING COMPOSITION

(71) Applicant: Kikkoman Corporation, Noda (JP)

(72) Inventor: Taro Horiba, Chiba (JP)

(73) Assignee: Kikkoman Corporation, Noda (JP)

( * ) Notice: Subject to any disclaimer, the term of this patent is extended or adjusted under 35 U.S.C. 154(b) by 129 days.

(21) Appl. No.: 16/775,216

(22) Filed: Jan. 28, 2020

(65) Prior Publication Data

US 2020/0164018 A1    May 28, 2020

Related U.S. Application Data

(62) Division of application No. 15/118,132, filed as application No. PCT/JP2014/080256 on Nov. 14, 2014, now abandoned.

(30) Foreign Application Priority Data

Feb. 14, 2014   (JP) ................. 2014-026763

(51) Int. Cl.
  *A61K 36/752*   (2006.01)
  *A61K 31/366*   (2006.01)
  *A61K 31/585*   (2006.01)

(52) U.S. Cl.
  CPC .......... *A61K 36/752* (2013.01); *A61K 31/366* (2013.01); *A61K 31/585* (2013.01); *A61K 2236/37* (2013.01)

(58) Field of Classification Search
  None
  See application file for complete search history.

(56) References Cited

U.S. PATENT DOCUMENTS

2006/0116509 A1 *   6/2006   Manners ................ C07H 1/06
                                                        536/127
2007/0237885 A1    10/2007   Jayaprakasha et al.

FOREIGN PATENT DOCUMENTS

| JP | 2001-158728 A | 6/2001 |
| JP | 2004-010480 A | 1/2004 |
| JP | 2007-297343 A | 11/2007 |
| JP | 2008-156294 A | 7/2008 |

OTHER PUBLICATIONS

Minamisawa et al., The functional evaluation of waste yuzu (*Citrus junos*) seeds, 2014, Food & Function, issue 2, pp. 1-19.*
Sulaiman et al., Efects of temperature, time, and solvent ratio on the extraction of phenolic compounds and the anti-radical activity of *Clinacanthus nutans* Lindau leaves by response surface , 2017, Chemical Central Journal, 11:54, pp. 1-11.*
Jay Basu, "The Production Method for Grapefruit Seed Extract (Citrus Grandis Seed Extract)", Natural Sourcing (2011).
Search Report for European Patent Application No. 14882573.0, dated Apr. 8, 2019.
Anonymous, "Yuzu Seed Extract For Whitening and beauty, Relaxation and metabolic syndrome" (Aug. 7, 2011), Dryza Oil & Fat Chemical Co., Ltd., http://www.oryza.co.jp/html/english/pdf/Yuzu_Seed_Extract_ver3.0M/pdf.
Anonymous, "Yuzu Seed Extract—For Beauty Enhancement and Relaxation" (Aug. 12, 2005), CELLBONE Technology, http://www.cellbone.com/Yuzu/htm.
Ozaki et al., "Limonoid Glucosides in Citrus Seeds", Agricultural and Biological Chemistry 55(1):137-141 (1991).
Herman et al., "Analysis of limonoids in citrus seeds", Modem Methods of Plant Analysis New Series vol. 14; Seed Analysis: 361-375 (1992).
Supplemental Partial Search Report for European U.S. Appl. No. 14/882,573 (dated Dec. 22, 2017).
Ono et al., "Anti-obesity and anti-hyperglycemic effects of the dietary citrus limonoid nomilin in mice fed a high-fat diet"; Biochemical and Biophysical Research Communications, 410(3):677-681 (2011).
Dzaki et al., "Ichangensin Glucoside in Citrus Junos, Citrus Sudachi an Citrus Sphaerocarpa," Phytochemistry, 30(8): 2659-2661 (1991).
Furutani et al., "Kankitsu Shushi ni Okeru Limonoid Rui ni Kansuru Kenkyu," Annual Meeting of JSBBA Koen Yoshishu, p. 12(2P0090B) (2009).
Morishita et al., "The Isolation of Limonoids of 'Banpeiyu' (*C. grandis* Osbeck)," Nihon Shokuhin Kogyo Gakkaishi, 32(8): 590-591 (1985).
Minamisawa et al., "The functional evaluation of waste yuzu (*Citrus junos*) seeds"; Food & Function, 5(2):330-336 (Nov. 21, 2013).
International Search Report for International Application No. PCT/JP2014/080256 dated Jan. 27, 2015.
Q. Tian et al.: "Isolation of Limonoids from Seeds of Citrus Sinensis", Chemistry and Industry of Forest Products, 19(3): 71-74 (1999).
Office Action for Chinese Patent Application No. 201480077486.7, dated Oct. 9, 2019.

* cited by examiner

*Primary Examiner* — Terry A McKelvey
*Assistant Examiner* — Catheryne Chen
(74) *Attorney, Agent, or Firm* — Merchant & Gould P.C.

(57) ABSTRACT

Provided are: a citrus seed extract-containing composition, a food and a drug all of which sufficiently exert a novel function of a citrus (specifically, a citrus seed extract), and a method for producing the citrus seed extract-containing composition. The citrus seed extract-containing composition includes obacunone and nomilin both derived from a citrus seed extract. Herein, the ratio of the obacunone content to the nomilin content (i.e., obacunone content/nomilin content) is at least 0.020.

2 Claims, 18 Drawing Sheets

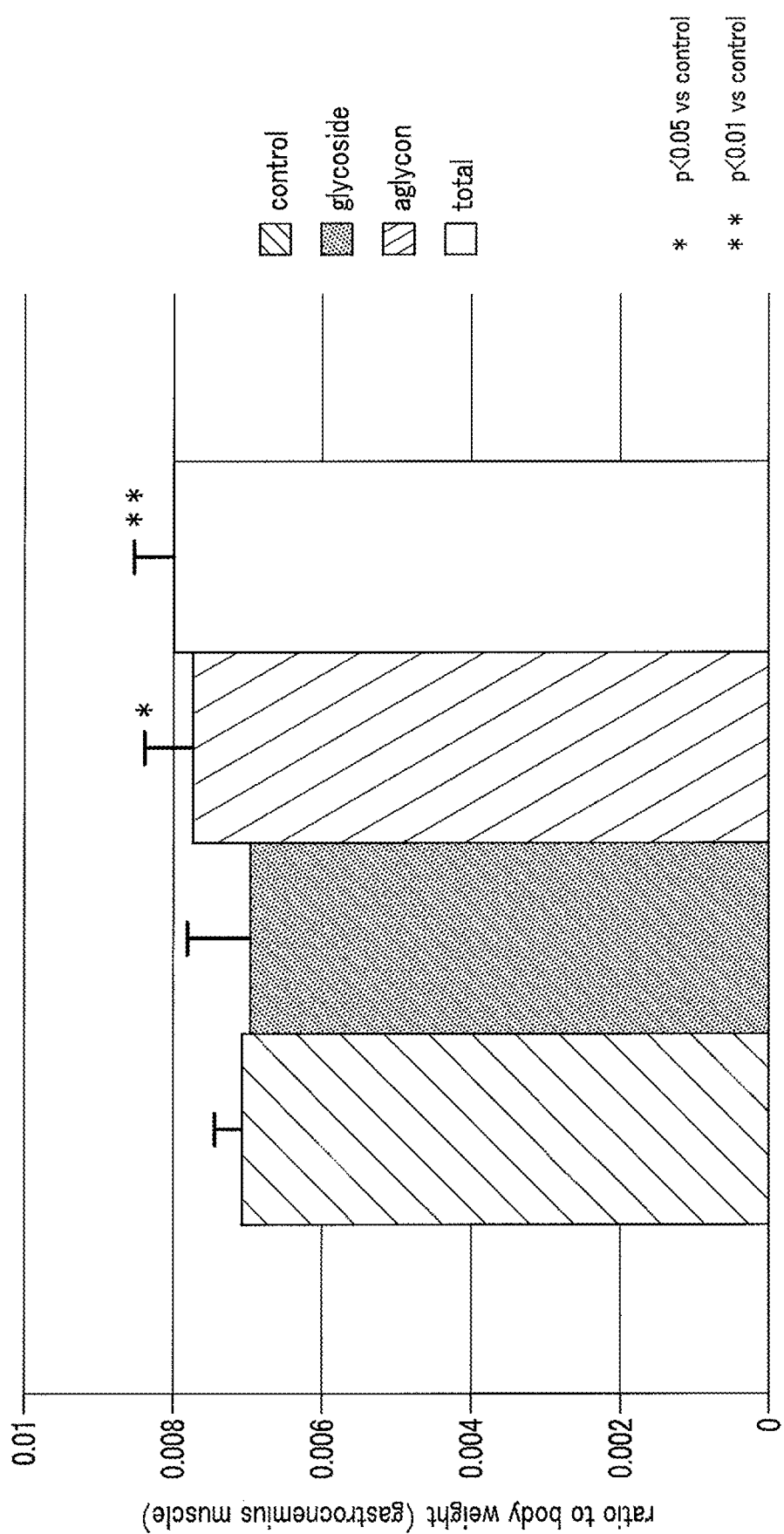

CITRUS SEED EXTRACT-CONTAINING COMPOSITION, FOOD, DRUG, AND METHOD FOR PRODUCING CITRUS SEED EXTRACT-CONTAINING COMPOSITION

This application is a Divisional of U.S. patent application Ser. No. 15/118,132, filed Oct. 21, 2016, which is a U.S. National Stage application under 35 U.S.C. § 371 of International Patent Application No. PCT/JP2014/080256, filed Nov. 14, 2014, which claims the benefit of priority to Japanese Patent Application No. 2014-026763, filed Feb. 14, 2014, the disclosures of all of which are hereby incorporated by reference in their entireties.

FIELD OF INVENTION

The present invention relates to a citrus seed extract-containing composition, a food, a drug, and a method for producing the citrus seed extract-containing composition. In particular, the present invention relates to a citrus seed extract-containing composition, a food and a drug all of which have a novel application, and a method for producing such a citrus seed extract-containing composition.

BACKGROUND

A citrus fruit (e.g., belonging to genus *Citrus*, genus *Poncirus* and genus *Fortunella* of family Rutaceae of order Sapindales) is widely applied around the world to a food for eating raw, juice, a confectionery material, and seasoning for cooking. Further, a citrus fruit is recognized as a food for promoting health because a citrus contains quantities of vitamin C and dietary fibers.

Among those citruses, especially Yuzu (botanical name: *Citrus junos*) is reported to have various excellent functions according to recent investigations.

For example, Patent Document 1 discloses that a Yuzu extract has a function for promoting productivity of hyaluronic acid. Further, Patent Document 2 discloses that a single-celled product of Yuzu has a function for peeling keratin.

In short, Patent Documents 1 and 2 disclose applications of Yuzu extracts (i.e., for promoting productivity of hyaluronic acid, and peeling keratin).

DOCUMENTS OF PRIOR ART

Patent Documents

Patent Document 1: Japanese Unexamined Patent Application Publication No. 2001-158728
Patent Document 2: Japanese Unexamined Patent Application Publication No. 2004-10480

SUMMARY OF INVENTION

Problems To Be Solved by Invention

However, an extract of citrus such as Yuzu may have a novel function hitherto undiscovered besides the functions disclosed in Patent Documents 1 and 2.

Further, there is a demand for not only discovering a novel function but also providing a highly useful composition sufficiently exerting the novel function. Specifically, the demand includes identifying an active ingredient which is contained inside a citrus (i.e., particularly, inside a citrus seed) and greatly exerts the novel function, and eventually discovering a method for collecting more quantities of such an active ingredient.

In view of the above, an object of the present invention is to provide a citrus seed extract-containing composition, a food and a drug all of which sufficiently exert the novel function of a citrus (particularly, a citrus seed), and a method for producing the citrus seed extract-containing composition.

Means for Solving Problems

The problem may be solved by the following aspects.

(1) A citrus seed extract-containing composition including obacunone and nomilin both derived from a citrus seed extract, in which a ratio of an obacunone content to a nomilin content (i.e., obacunone content/nomilin content) is at least 0.020.

(2) A citrus seed extract-containing composition described in the aspect (1) in which the ratio of the obacunone content to the nomilin content (i.e., obacunone content/nomilin content) is at least 0.100.

(3) A citrus seed extract-containing composition described in the aspect (1) or (2), in which the ratio of the obacunone content to the nomilin content (i.e., obacunone content/nomilin content) is at least 0.300.

(4) A citrus seed extract-containing composition described in any one of the aspects (1)-(3), in which the citrus seed extract is a Yuzu seed extract.

(5) A citrus seed extract-containing composition described in the aspects (1)-(4), which is usable for lowering a blood-glucose level.

(6) A citrus seed extract-containing composition described in the aspects (1)-(5), which is usable for increasing a skeletal muscle quantity.

(7) A citrus seed extract-containing composition described in the aspects (1)-(6), which is usable for reducing a body fat.

(8) A food containing a citrus seed extract-containing composition described in any one of the aspects (1)-(7).

(9) A drug containing a citrus seed extract-containing composition described in any one of the aspects (1)-(8) as an active ingredient.

(10) A method for producing a citrus seed extract-containing composition, including the steps of heating citrus seeds at 60° C. or more, and extracting a citrus seed extract from the citrus seeds thus heated.

(11) A method for producing a citrus seed extract-containing composition described in the aspect (10), in which the citrus seeds are heated at 100° C. or more in the heating step.

(12) A method for producing a citrus seed extract-containing composition described in the aspect (10) or (11), in which the citrus seeds are heated for at least 5 min in the heating step.

(13) A method for producing a citrus seed extract-containing composition described in any one of the aspects (10)-(12), in which the citrus seeds is Yuzu seeds.

Effect of Invention

In a citrus seed extract-containing composition of the present invention, a ratio of the obacunone content to the nomilin content is set to at least a predetermined value, whereby a much quantity of obacunone is included therein. Accordingly, the citrus seed extract-containing composition of the present invention may sufficiently exert novel functions (e.g., lowering a blood-glucose level, increasing a skeletal muscle quantity and reducing a body fat).

A food and a drug of the present invention may sufficiently exert novel functions (e.g., lowering a blood-glucose level, increasing a skeletal muscle quantity and reducing a body fat) by containing a citrus seed extract-containing composition having a much quantity of obacunone.

A method for producing a citrus seed extract-containing composition of the present invention may sufficiently exert novel functions (e.g., lowering a blood-glucose level, increasing a skeletal muscle quantity and reducing a body fat) by including the step of heating citrus seeds at a predetermined temperature or more, allowing a much quantity of obacunone to be included in the citrus seed extract-containing composition.

BRIEF DESCRIPTION OF DRAWINGS

FIG. 5 shows measured data illustrating a weight ratio of a gastrocnemius muscle to a body of KKAy mice at the day 28 after initiating the rearing experiment.

EMBODIMENTS FOR CARRYING OUT INVENTION

Figure 1:
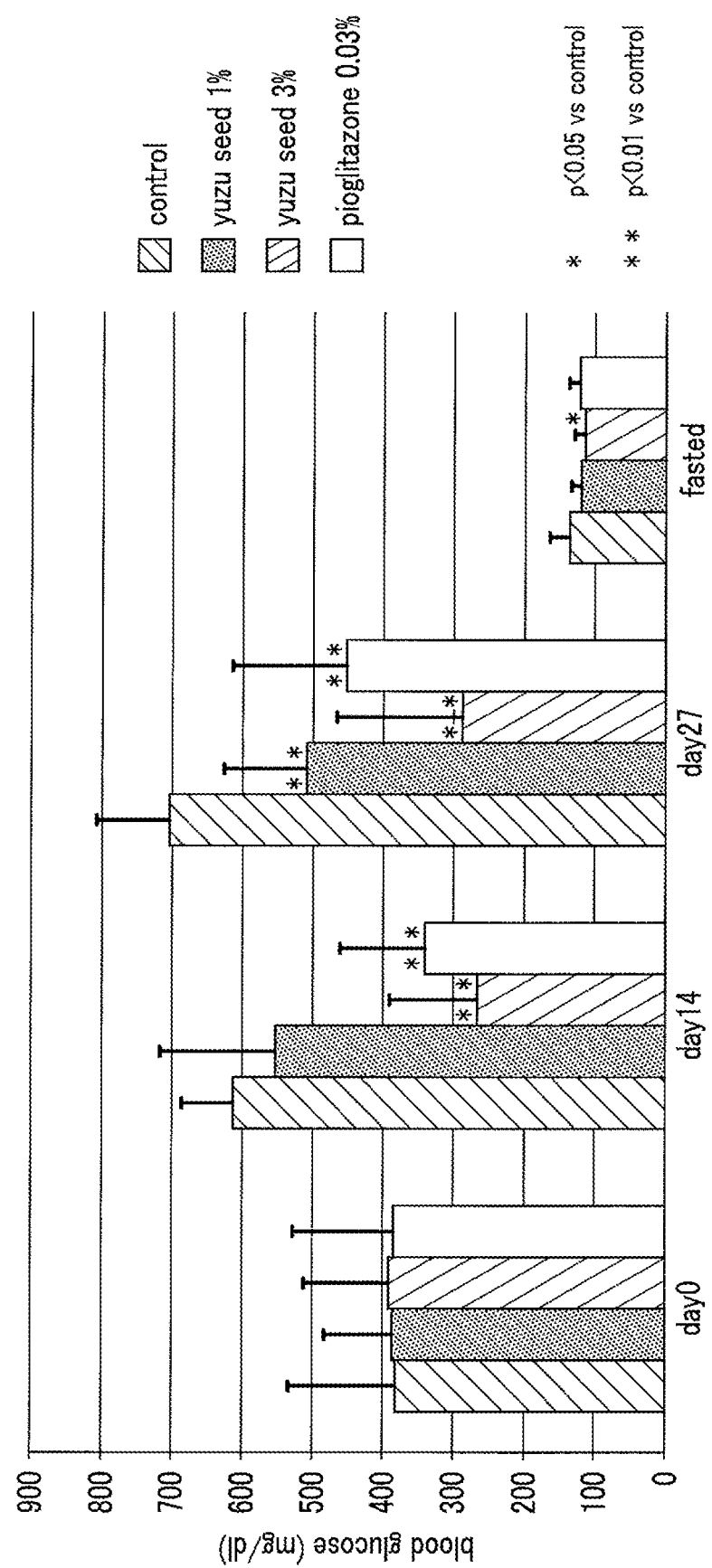
FIG. 1 shows measured data illustrating changes in blood-glucose levels of KKAy mice.

Hereinafter, embodiments of a citrus seed extract-containing composition, a food, a drug, and a method for producing the citrus seed extract-containing composition of the present invention will be described in detail.

<<Citrus Seed Extract-Containing Composition>>

A citrus seed extract-containing composition of the present embodiment (hereinafter, appropriately referring to as the "composition") includes obacunone and nomilin both derived from a citrus seed extract, in which a ratio of a obacunone content to a nomilin content is set to at least a predetermined value.

Hereinafter, first, the citrus seed extract and applications thereof will be described, and secondly components of the composition will be further described in detail, with respect to the composition of the present embodiment.

[Citrus Seed Extract]

A citrus seed is a seed of plant belonging to genus *Citrus*, genus *Poncirus* and genus *Fortunella* of family Rutaceae of order Sapindales. A citrus seed extract is an extract obtained via extraction from the above seeds.

Specifically, a citrus includes Yuzu of genus *Citrus* of family Rutaceae (botanical name: *Citrus junos*), Lemon of genus Citrus of family Rutaceae (botanical name: Citrus limon), Grapefruit of genus *Citrus* of family Rutaceae (botanical name: *Citrus X paradisi*).

Here, when the inventors checked compositions in various parts of a plurality of fruits belonging to a citrus, it was confirmed that considerable quantities of a limonoid aglycone, which enhances functions for lowering a blood-glucose level, increasing a skeletal muscle quantity and reducing a body fat, were included in a citrus, especially, in an extract of the citrus seeds.

Hereby, considerable quantities of the limonoid aglycone can be obtained from a small quantity of a raw material (e.g., Yuzu seed, Lemon seed, and Grapefruit seed etc.). Thus, use of the limonoid aglycone in the citrus seed extract can suppress a quantity of a raw material thus used, leading to cost and time reduction of the extraction in the production process.

[Applications]

A novel application of a citrus seed extract-containing composition of the present embodiment includes the following ones.

(Application to Lowering of Blood-Glucose Level)

An application to lowering of a blood-glucose level is that the composition is used for lowering a blood-glucose and an HbA1c level, more specifically, fora hypoglycemic agent, a hypoglycemic food (i.e., health food) and a hypoglycemic drug.

Herein, HbA1c represents a value calculated by a ratio of a quantity of hemoglobin stably bonding with glucose at the N-terminus valine in the β-chain to a total quantity of hemoglobin.

(Application to Increase in Skeletal Muscle Quantity)

An application to increase in a skeletal muscle quantity is that the composition is used for increasing a quantity of a skeletal muscle, more specifically, a skeletal muscle increasing agent, a skeletal muscle increasing food (i.e., health food) and a skeletal muscle increasing drug.

Here, the skeletal muscle is one class of muscles, representing a muscle for moving a skeleton. The skeletal muscle includes, for example, a gastrocnemius muscle.

(Application to Reduction of Body Fat)

An application to reduction of a body fat is that the composition is used for reducing a quantity of a body fat, more specifically, for a body fat reducing agent, a body fat reducing food (i.e., health food) and a body fat reducing drug.

Here, the body fat (i.e., adipose tissue) includes, for example, a perirenal fat, a mesenterium fat, an epididymis fat and a subcutaneous fat or the like.

[Components of Composition]

A composition of the present embodiment includes a limonoid aglycone and a limonoid glycoside both derived from a citrus seed extract.

[Limonoid Aglycone]

A limonoid aglycone is a group of chemical substances derived from a citrus seed extract (i.e., substances included in citrus seed extract) and having a chemical structure of a furanolactone skeleton.

Further, limonoid of the limonoid aglycone is a phytochemical largely included in a citrus plant, and a chemical substance having a chemical structure of a furanolactone. Herein, an aglycone of the limonoid aglycone represents a moiety of a glycoside formed by removing glucose from the glycoside.

Moreover, the limonoid aglycone is limonin, nomilin, deacetylnomilin or obacunone described as follows.

(Limonin)

Limonin ($C_{26}H_{30}O_8$) is represented by the following structural formula.

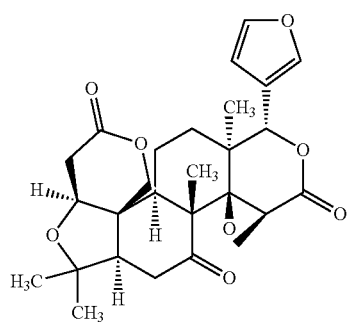

(Nomilin)

Nomilin ($C_{28}H_{34}O_9$) is represented by the following structural formula.

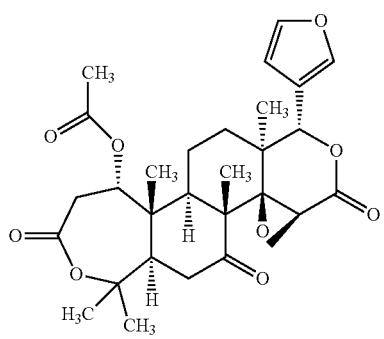

(Deacetylnomilin)

Deacetylnomilin ($C_{26}H_{32}O_8$) is represented by the following structural formula.

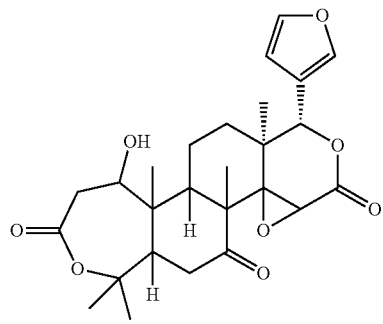

(Obacunone)

Obacunone ($C_{26}H_{30}O_7$) is represented by the following structural formula.

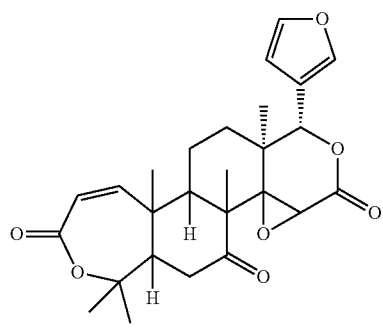

[Content Ratio of Obacunone]

In the composition of the present embodiment, a ratio of the obacunone content to the nomilin content (i.e., obacunone content/nomilin content: hereinafter, properly referring to as a "content ratio of obacunone") is set to at least 0.020.

Among the limonoid aglycones described above, especially, obacunone may exert the functions for lowering a blood-glucose level, increasing a skeletal muscle quantity and reducing a body fat quantity, even with the extremely small amount thereof. When the content ratio of obacunone in the composition of the present embodiment is at least 0.020, such obacunone may sufficiently exert the respective functions described above. Herein, the content ratio of obacunone is preferably at least 0.100, most preferably at least 0.300 in order to surely exert the respective functions described above.

Here, an upper limit of the content ratio of obacunone is not particularly limited. However, the content ratio is 5.000 or less according to the method for producing the composition of the present embodiment described hereinafter.

Further, obacunone may be included at preferably 0.001-10 mass %, more preferably 0.005-5 mass % in a solid substance of the citrus seed extract-containing composition.

A content ratio of obacunone and an obacunone content of the present embodiment may be controlled by a treatment in the heating step described hereinafter.

[Limonoid Glycoside]

A limonoid glycoside is a group of chemical substances derived from a citrus seed extract (i.e., substances included in a citrus seed extract). In the limonoid glycoside, glucose is bonded to the above described limonoid aglycone (i.e., via glycosidic bond).

[Other Contents]

The composition of the present embodiment may include a saccharide as an extraction residue besides the above described limonoid aglycone and limonoid glycoside.

Further, the composition of the present embodiment may be prepared in a powder form, a granule from, a fine granule form, a paste form, a gel form, a solid form, a capsule form or a liquid form.

Moreover, the composition of the present embodiment may be simply a composition containing a citrus extract. Thus, the composition of the present embodiment may be composed of a citrus extract alone.

A dosage of the composition of the present embodiment may be appropriately set depending on a target application, an age and weight of target. For example, a typical dosage of obacunone as a dried material may be in the range of 0.1-2,000 mg/kg, preferably 2-300 mg/kg per day per adult human. Note, obacunone may be administered in a single dosage or in dosage divided several times.

Next, a food including the above described citrus seed extract-containing composition of the present embodiment will be described in detail.

<<Food>>

A food of the present embodiment includes the above described composition and is usable fora health food for lowering a blood-glucose level, increasing a skeleton muscle quantity, and reducing a body fat.

Herein, a food of the present embodiment includes, for example, confectionary, bread, milk, various kinds of beverage, udon (i.e., Japanese wheat noodle), soba (i.e., buckwheat noodle), pasta, cooked rice, seasoning, spice, daily dish, fat-containing food, liquor, soft drink or the like. Note, a food of the present embodiment is produced by blending various compositions known to a skilled person in the art depending on a type of the food described above.

Next, a drug including the above described citrus seed extract-containing composition of the present embodiment as an active ingredient will be described in detail.

<<Drug>>

A drug of the present embodiment includes the above described composition as an active ingredient, and is usable for lowering a blood-glucose level, increasing a skeleton muscle quantity and reducing a body fat.

Further, in a drug of the present embodiment, the above described composition may be preferably formulated in combination with a pharmaceutical carrier such as a suitable excipient following a conventional method in order to improve drug controllability, or absorbability when the drug is administered to a living body. Herein, an oral administration drug is produced in a capsule form, a tablet form, a granule form, a fine granule form, a syrup form, a dry syrup form or the like. A parenteral administration drug includes a percutaneous absorption agent such as an ointment, a percutaneous tape, an injection agent, a suppository, a pessary, an aerosol agent or the like.

Next, a method for producing a citrus seed extract-containing composition, a food, and a drug of the present embodiment will be described in detail.

<<Method for Producing Citrus Seed Extract-Containing Composition>>

Figure 17:
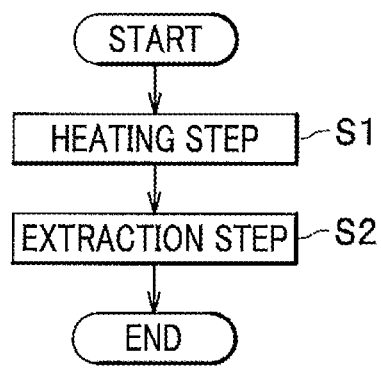
FIG. 17 is a flowchart describing a method for producing a citrus seed extract-containing composition of the present invention.

As shown in FIG. 17, a method for producing a citrus seed extract-containing composition includes a heating step S1 and an extraction step S2. Further, the method for producing the composition of the present embodiment may include a grinding step as described hereinafter.

(Heating Step)

A heating step S1 is the step of heating citrus seeds.

Here, a heating temperature in the heating step S1 is at 60° C. or more, preferably 100° C. or more. When the citrus seeds are heated at a predetermined temperature or more, obacunone may be generated in the citrus sees, thereby increasing the obacunone content. Accordingly, the composition containing an extract thus extracted from the citrus seeds may sufficiently exert the functions for lowering a blood-glucose level, increasing a skeletal muscle quantity and reducing a body fat.

An upper limit of the heating temperature in the heating step S1 is not specifically limited. However, when the temperature reaches more than 150° C., a quantity of a limonoid aglycone having obacunone is decreased, causing a disadvantage. In view of the above, the heating temperature is preferably set at 150° C. or less, most preferably 140° C. or less.

Here, the heating step S1 is not specifically limited as long as S1 is the step of heating citrus seeds. However, S1 may be also the step of drying citrus seeds via heat, namely, the drying step. Further, S1 may be the step of heat-drying citrus seeds without performing humidification.

Moreover, in the heating step S1, when the citrus seeds become dry by heating the citrus seeds at a predetermined temperature, a condition (i.e., state) of the citrus seeds thus heated may be kept substantially constant. As a result, the extraction condition in the extraction step S2 described hereinafter may be easily set, and simultaneously quality of the composition finally obtained may be kept stable.

Here, the heating temperature described above is specifically a temperature measured in the heating environment (i.e., in the environment atmosphere) of the heating step S1. Here, in the heating step S1, the temperature of the targeted citrus seeds is almost the same as in the heating environment.

When a heating-period in the heating step S1 is set to at least 5 min, preferably at least 10 min, more preferably at least 30 min, the effect of increasing the obacunone content inside the citrus seeds may be sufficiently exerted. Herein, even when a heating-period is set to more than 1440 min, the obacunone content is hardly increased, and further a content of a limonoid aglycone other than obacunone is decreased. In view of the above, the heating-period may be set within 1440 min, preferably within 720 min, most preferably within 360 min.

Here, a treatment method in the heating step S1 may be performed by known methods such as a method for placing the citrus seeds in the environment at the predetermined temperature or more thus described above (e.g., in dry furnace), and a method for blowing warm air onto the citrus seeds.

(Grinding Step)

A grinding step is the step of grinding the citrus seeds. A grinding method in the grinding step is not specifically limited, and may be performed by known methods using a mill or the like.

The grinding step is conducted after the heating step S1 and before the extraction step S2 as described hereinafter. However, the grinding step may be conducted before the heating step S1.

(Extraction Step)

An extraction step S2 is the step of extracting an extract from the citrus seeds.

An extraction treatment in the extraction step S2 is a treatment for extracting an extract from the citrus seeds obtained after the heating step S1 (or after grinding step) via using a polar solvent.

A temperature of extraction using a polar solvent in the extraction step S2 is from about 0° C. to a boiling point of the polar solvent, typically an ambient temperature. For example, when ethanol is used as a polar solvent, the extraction temperature is preferably set in the range from 0° C. to less than 70° C., more preferably from 5° C. to 60° C., in view of the extraction efficiency. Alternatively, when water is used as a polar solvent, the extraction temperature is preferably set in the range from 0° C. to 100° C., more preferably from 25° C. to 100° C., in view of the extraction efficiency.

An extraction period in the extraction step S2 is preferably from 1 min to 24 hr. However, the extraction may be performed for a period longer than 24 hr. Further, the extraction may be performed by any procedure of leaving at rest, stirring or the like.

In the extraction treatment in the extraction step S2, for example, a citrus seed extract may be obtained by adding a 1 to 50-fold volume, preferably a 5 to 20-fold volume of a polar solvent to the citrus seeds, to perform the extraction. Then, the resulting citrus seed extract may be diluted, condensed, dried and purified appropriately following a conventional method. Accordingly, a citrus seed extract-containing composition may be obtained.

A polar solvent used in the extraction step S2 is not specifically limited. Hereby, the polar solvent may include one kind of solvent or a plurality kinds of solvents selected from, for example, acetone, ethanol, ethyl methyl ketone, glycerin, ethyl acetate, methyl acetate, diethyl ether, cyclohexane, dichloromethane, editable fat and oil, 1,1,1,2-tetrafluoroethane, 1,1,2-trichloroethene, 1-butanol, 2-butanol, 1-propanol, 2-propanol, propylene glycol, hexane, water, methanol or the like.

Among the above solvents, a preferably usable solvent may include one selected from the group of ethanol (from 10 volume % to 100 volume %), methanol (from 10 volume % to less than 99.5 volume %), 1-butanol (from 30 volume % to less than 99.5 volume %), hexane (from 5 volume % to less than 70 volume %) and water. More preferably, such a usable solvent is ethanol or water, most preferably ethanol.

For example, an ethanol-containing solvent in the range from 10 volume % to 100 volume % may be used as a polar solvent. Preferably, such an ethanol-containing solvent in the range from 50 volume % to 100 volume %, and more preferably at about 70 volume % may be used. Note, the ethanol-containing solvent at 70 volume % means a mixture of water and ethanol set at the volume ratio of 3:7.

A citrus seed extract-containing composition of the present embodiment is preferably an organic solvent extract from the citrus seeds as describe above, more preferably an alcohol extract from the citrus seeds, and most preferably an ethanol extract from citrus seeds.

Herein, a method for producing a food and a drug of the present embodiment may include the steps of mixing the citrus seed extract-containing composition thus prepared as above with materials of the food and the drug, and subsequently producing the food and the drug following a conventional method for producing a food and a drug known by a skilled person in the art.

EXAMPLES

Next, Examples satisfying the requirements of the present embodiment, and Comparative Examples unsatisfying the requirements will be exemplified. Based on the descriptions of Examples and Comparative Examples, a citrus seed extract-containing composition, a food and a drug of the present invention will be explained in detail.

First, referring to Experiments 1-3, how a Yuzu seed extract and a limonoid aglycone exert the functions for lowering a blood-glucose level, increasing a skeleton muscle quantity and reducing a body fat will be explained.

Next, referring to Experiment 4, how a compound composing a limonoid aglycone is identified will be explained.

Further, referring to Experiment 5, how obacunone among the limonoid aglycones sufficiently exerts the function for lowering a blood-glucose level will be explained.

Moreover, referring to Experiment 6, how the temperature and the period of heat-drying Yuzu seeds influence a relative quantity and a content ratio of obacunone will be explained.

Finally, referring to Experiment 7, when citrus seeds other than Yuzu seeds are used, how the heat-drying process influences the generation of obacunone will be explained.

Experiment 1

Animal Experiments of KKAy Mice
(Blood-Glucose and HbA1c Levels)

(Conditions of Rearing Experiment)

KKAy mice at 3 weeks of age were purchased from CLEA Japan, Inc. as diabetes onset mode mice, and experimentally reared after preliminary rearing for 7 days. Herein, the conditions of rearing the mice were as follows. Temperature: $23\pm1°$ C.; Humidity: $55\pm10\%$; Lighting: during 7 am to 7 pm (lights out for other period); Free intake of water and feed.

(Composition of Experimental Feed)

AIN-93G was used for base experimental feed. 1 mass % or 3 mass % of the Yuzu seed extract, or 0.03 mass % of pioglitazone was mixed to AIN-93G, and the mixture was administered to the mice.

Note, the Yuzu seed extract used in Experiment 1 was prepared by heat-drying the Yuzu seeds at 100° C. for 720 min, subsequently grinding the dried Yuzu seeds so that the particle size (i.e., diameter) became about 1 mm or less, and performing extraction at an ambient temperature for 10 min using 10-fold volume of 100% ethanol to the ground Yuzu seeds.

(Method for Collecting Experimental Data)

In each of a control group (i.e., administered with AIN-93G alone including no other materials), a Yuzu seed extract (1% mass %) added group, a pioglitazone (0.03 mass %) added group, 10 mice were preliminarily reared for 7 days, and subsequently reared with the experimental feed totally for 28 days.

After initiating the rearing experiment, blood was collected through a tail vain at the time from 9 am to 11 am at a day after the predetermined days passed. Then, the collected blood was analyzed by blood-glucose analyzers (HORIBA, Ltd. Antsence III and Bayer DCA2000) to measure a blood-glucose level and an HbA1c level. The measured blood-glucose and HbA1c levels were processed to calculate the mean value of each group.

Note, all the HbA1c levels thus measured and calculated in the experiment are represented by the JDS values.

Figure 2:
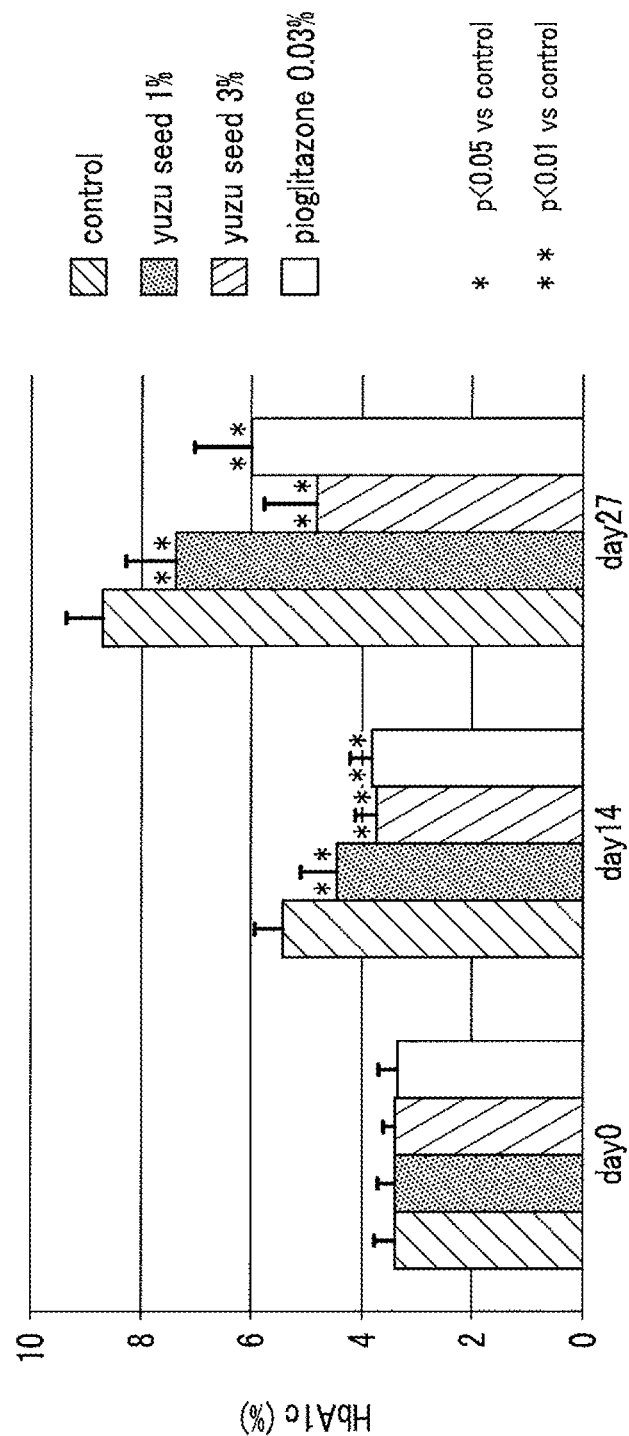
FIG. 2 shows measured data illustrating changes in HbA1c levels of KKAy mice.

FIG. 1 shows changes in blood-glucose levels of the KKAy mice administered with experimental feed. FIG. 2 shows changes in HbA1c levels of the KKAy mice administered with the experimental feed. Here, the ordinate of FIG. 1 represents blood-glucose levels (mg/dl) and the ordinate of FIG. 2 represents HbA1c levels, while the abscissas of FIGS. 1 and 2 represent the number of days (day) having passed after the rearing experiment was initiated.

Here, the term of "P<0.01 vs control" means that the p value is smaller than 0.01 against the control group.

(Analysis of Experimental Data)

As shown in the date of FIG. 1, it is revealed that blood-glucose levels of the control group were increased as the number of days was increased, while the blood-glucose levels in the Yuzu seed extract added group were suppressed and eventually decreased. Further, the effect of lowering a blood-glucose level was sufficiently confirmed by the data of the Yuzu seed extract (1 mass %) added group.

Particularly, the data of the Yuzu seed extract (3% mass) added group demonstrated that the blood-glucose levels at the days 14 and 27 were lower than the levels at the day 0, and further the effect of lowering a blood-glucose level of the Yuzu seed extract (3% mass) added group was equal to or greater than the effect of the pioglitazone administered group.

As shown in the data of FIG. 2, it was confirmed that HbA1c levels were decreased in the Yuzu seed extract added groups. The data of the Yuzu seed extract (1 mass % and 3 mass %) added groups sufficiently demonstrated the effect of lowering HbA1c levels.

As mentioned above, it was confirmed that the citrus seed (i.e., Yuzu seed) extract-containing composition of the present invention exerted not only the effect of lowering a blood-glucose level under an ordinary condition but also the effect of lowering a blood-glucose level even under a chronic hyperglycemia condition.

Experiment 2

Animal Experiments of KKAy Mice
(Blood-Glucose and HbA1c Levels)

Conditions of rearing experiments and a method for collecting experimental data were the same as in Experiment 1 (but 8 or 9 mice used in each group)

(Composition of Experimental Feed)

Basically, the same experimental feed as in Experiment 1 was used. However, besides the feed containing a Yuzu seed extract in the experimental feed (i.e., 3 mass % in the feed), other types of feed containing a limonoid aglycone or a limonoid glycoside (both types of feed were prepared so that the intake became equal to that in the Yuzu seed extract added group) were also used.

Here, the limonoid aglycone and the limonoid glycoside were obtained by fractionation of the Yuzu seed extract thus prepared in the same method as in Experiment 1.

Figure 3:
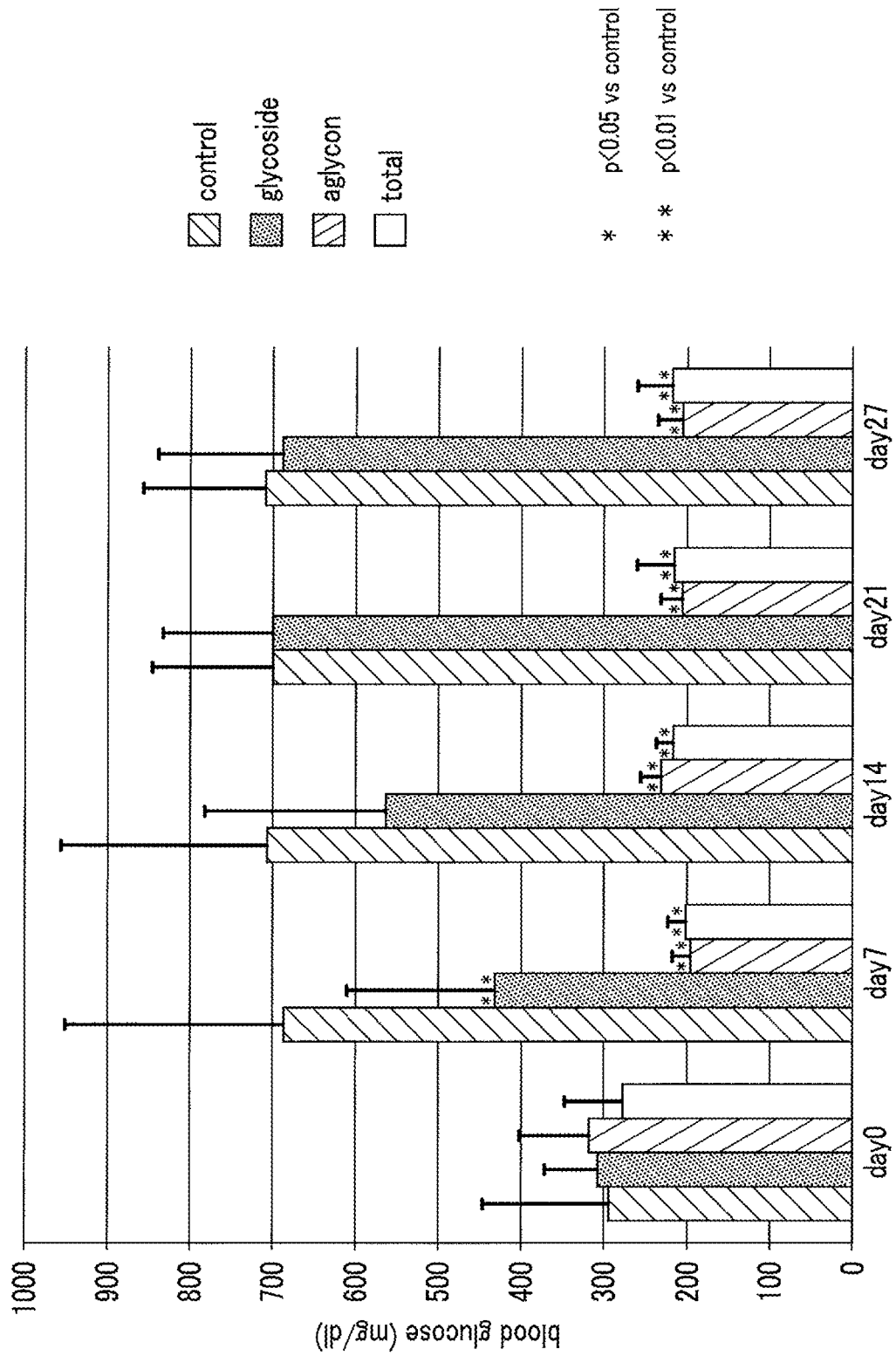
FIG. 3 shows measured data illustrating changes in blood-glucose levels of KKAy mice.
Figure 4:
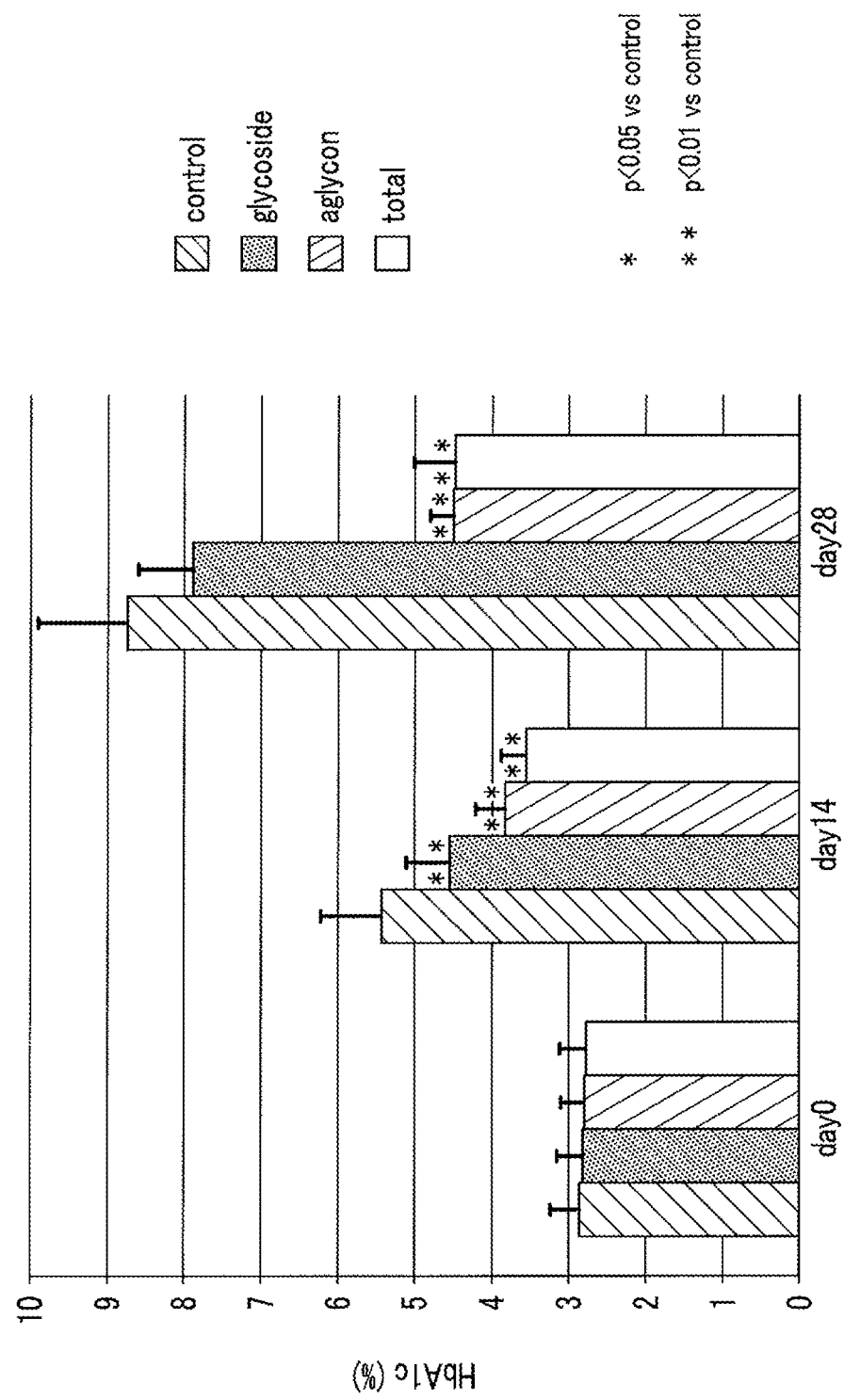
FIG. 4 shows measured data illustrating changes in HbA1c levels of KKAy mice.

FIG. 3 shows changes in blood-glucose levels of the KKAy mice administered with experimental feed, and FIG. 4 shows changes in HbA1c levels of the KKAy mice administered with the experimental feed. Here, the ordinate of FIG. 3 represents blood-glucose levels (mg/dl) and the ordinate of FIG. 4 represents HbA1c levels, while the abscissas of FIGS. 3 and 4 represent the number of days (day) having passed after the rearing experiment was initiated.

(Analysis of Experimental Data)

As shown in the data of FIG. 3, in the limonoid glycoside added group, the increase in the blood-glucose levels was partially suppressed compared to that in the control group at the day 7, while the blood-glucose levels became almost equal to those in the control group as the number of days was increased.

On the other hand, in the limonoid aglycone added group, the blood-glucose levels were greatly lowered compared to those in the control group after the day 7. Further, in the limonoid aglycone added group, the blood-glucose levels were almost equal to those in the Yuzu seed extract added group (i.e., total in FIG. 3).

As shown in the data of FIG. 4, in the limonoid aglycone added group, it was confirmed that the increase in the HbA1c levels was greatly suppressed compared to that in the control group and the limonoid glycoside added group at the day 28, and the HbA1c levels were eventually lowered. Further, in the limonoid aglycone added group, the HbA1c levels were almost equal to those in the Yuzu seed extract added group (i.e., total in FIG. 4).

Accordingly, it was confirmed that among the citrus seed (i.e., Yuzu seed) extract-containing compositions of the present embodiment, mainly the limonoid aglycone exerted the effect of lowering a blood-glucose level in animal blood, and simultaneously the effect of lowering a blood-glucose level under a chronic hyperglycemia condition.

Experiment 3

Animal Experiments of KKAy Mice (Increase in Skeleton Muscle Quantity and Reduction of Body Fat)

(Method for Collecting Experimental Data)

In each of a control group, a limonoid glycoside added group, a limonoid aglycone added group and a Yuzu seed extract added group, 8 or 9 mice were preliminarily reared for 7 days, and reared totally for 28 days with experimental feed.

For checking changes in a quantity of a skeleton muscle, measured was a weight ratio of a "gastrocnemius muscle" to a mouse body of the respective mice at the day 28 after initiation of the rearing experiment (i.e., gastrocnemius muscle weight/mouse body weight).

Further, for observing changes in a quantity of a body fat, respective weight ratios of a "perirenal fat", a "mesenterium fat", an "epididymis fat" and a "subcutaneous fat" to a mouse body (i.e., weight of each fat (g)/weight of mouse body (g)) were measured.

Then, mean values of the respective weight ratios of the above described muscle and fats thus measured in the respective groups were calculated.

Herein, the weights of the above described muscle and fats were measured by removing the respective tissues, washing the removed tissues with saline, and excluding water therefrom with sanitary cotton.

Figure 6A:
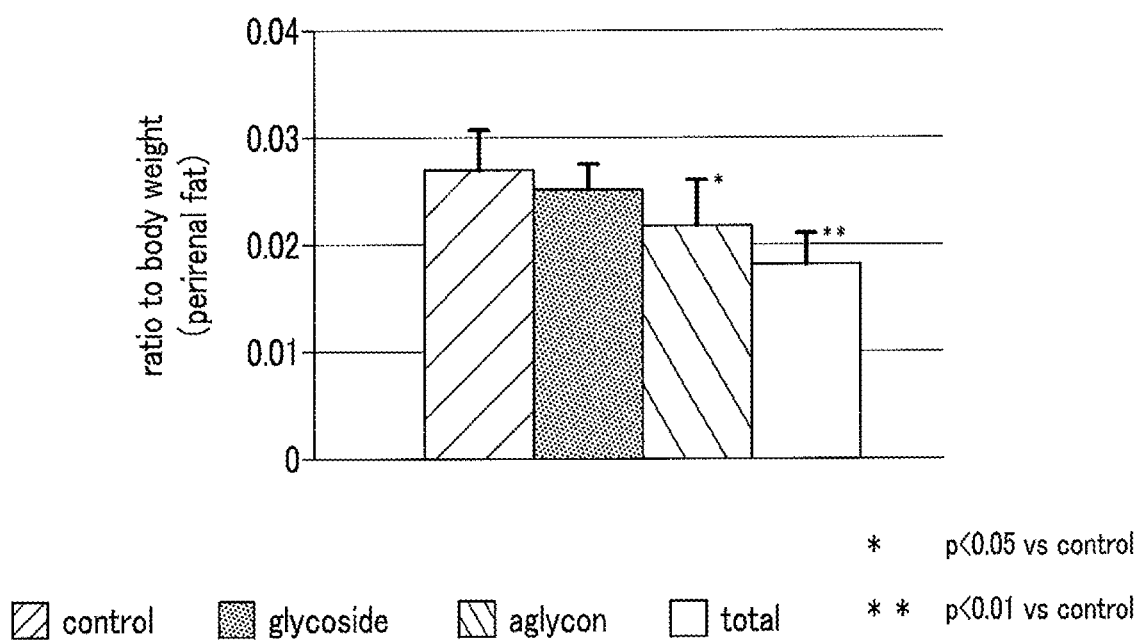
FIG. 6A shows measured data illustrating a weight ratio of a perirenal fat to a body of KKAy mice at the day 28 after initiating the rearing experiment.
Figure 6B:
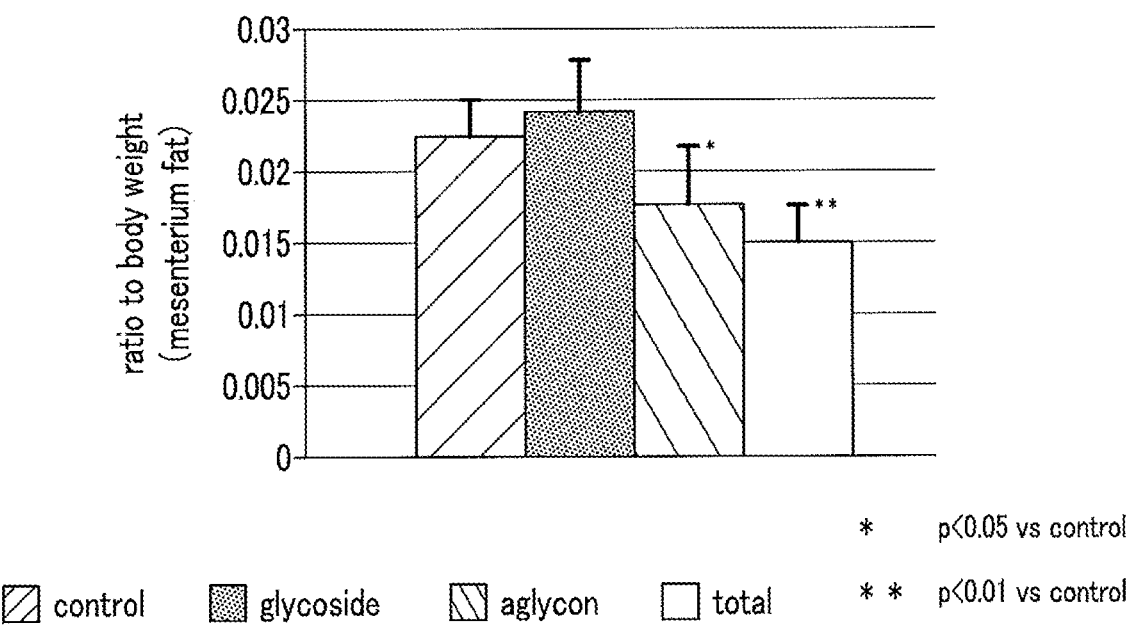
FIG. 6B shows measured data illustrating a weight ratio of a mesenterium fat to a body of KKAy mice at the day 28 after initiating the rearing experiment.
Figure 6C:
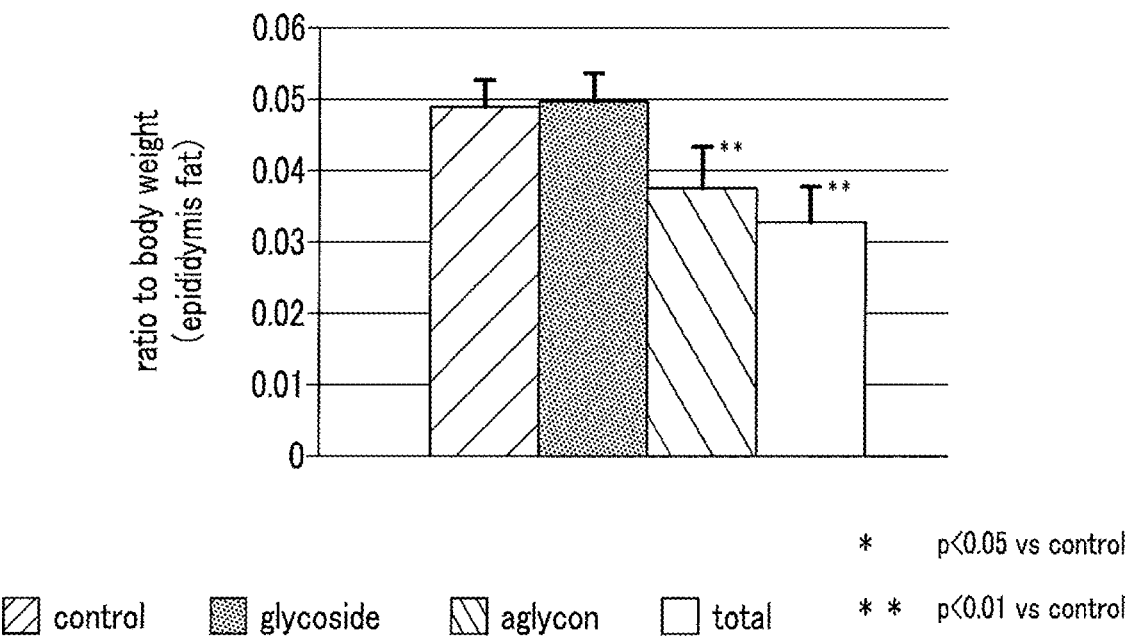
FIG. 6C shows measured data illustrating a weight ratio of an epididymis fat to a body of KKAy mice at the day 28 after initiating the rearing experiment.
Figure 6D:
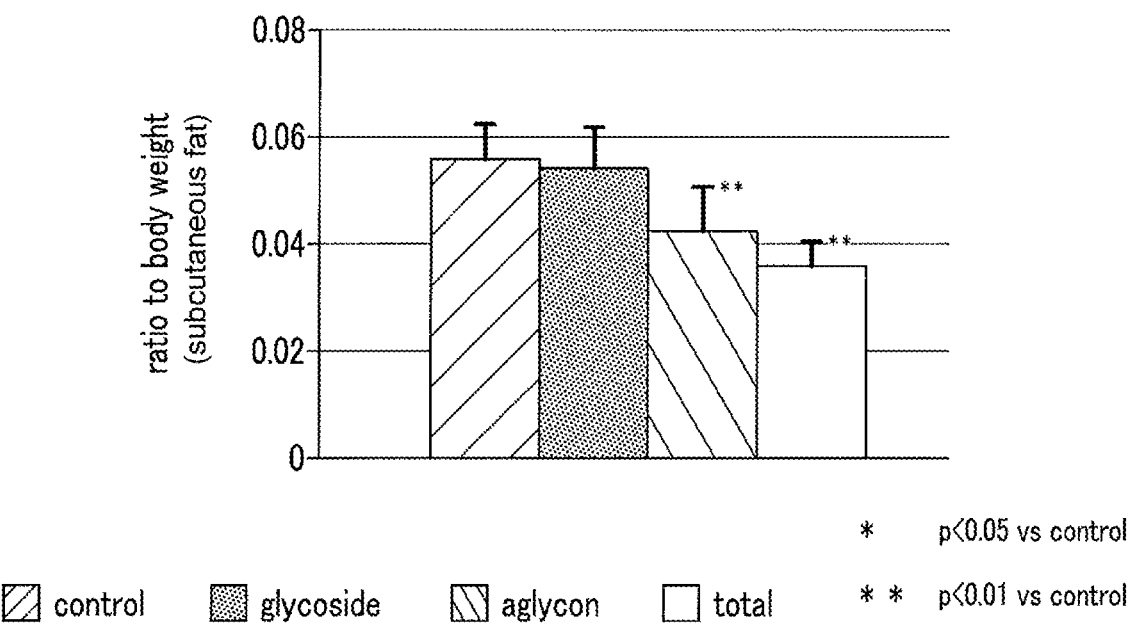
FIG. 6D shows measured data illustrating a weight ratio of a subcutaneous fat to a body of KKAy mice at the day 28 after initiating the rearing experiment.

FIG. 5 shows a weight ratio of a gastrocnemius muscle to a mouse body of the mice at the day 28 after initiation of the rearing experiment. Further, FIGS. 6A, 6B, 6C and 6C show respective weight ratios of a perirenal fat, a mesenterium fat, an epididymis fat and a subcutaneous fat to a mouse body of the mice at the day 28 after initiation of the rearing experiment.

(Analysis of Experimental Data)

As shown in the data of FIG. 5, in the limonoid aglycone added group, a weight ratio of the gastrocnemius muscle was increased.

As shown in the data of FIGS. 6A, 6B, 6C and 6D, in the limonoid aglycone added groups, all the weight ratios of the perirenal fat, the mesenterium fat, the epididymis fat and the subcutaneous fat were reduces.

Accordingly, it was confirmed that among the citrus seed (i.e. Yuzu seed) extraction-containing compositions, mainly the limonoid aglycone exerted the effect of increasing the quantity of the skeleton muscle as well as the effect of reducing the body fat.

Experiment 4

Limonoid Aglycone Contained in Citrus Seed Extract

The limonoid aglycone thus obtained in Experiment 3 was fractionated by a silica-gel column (daisogel 1002A IR60-40/63A), and four types of limonoid aglycones were obtained. Those samples were subjected to LC-MS analysis following a conventional method. The resulting data are shown in FIGS. 7-10.

Figure 7:
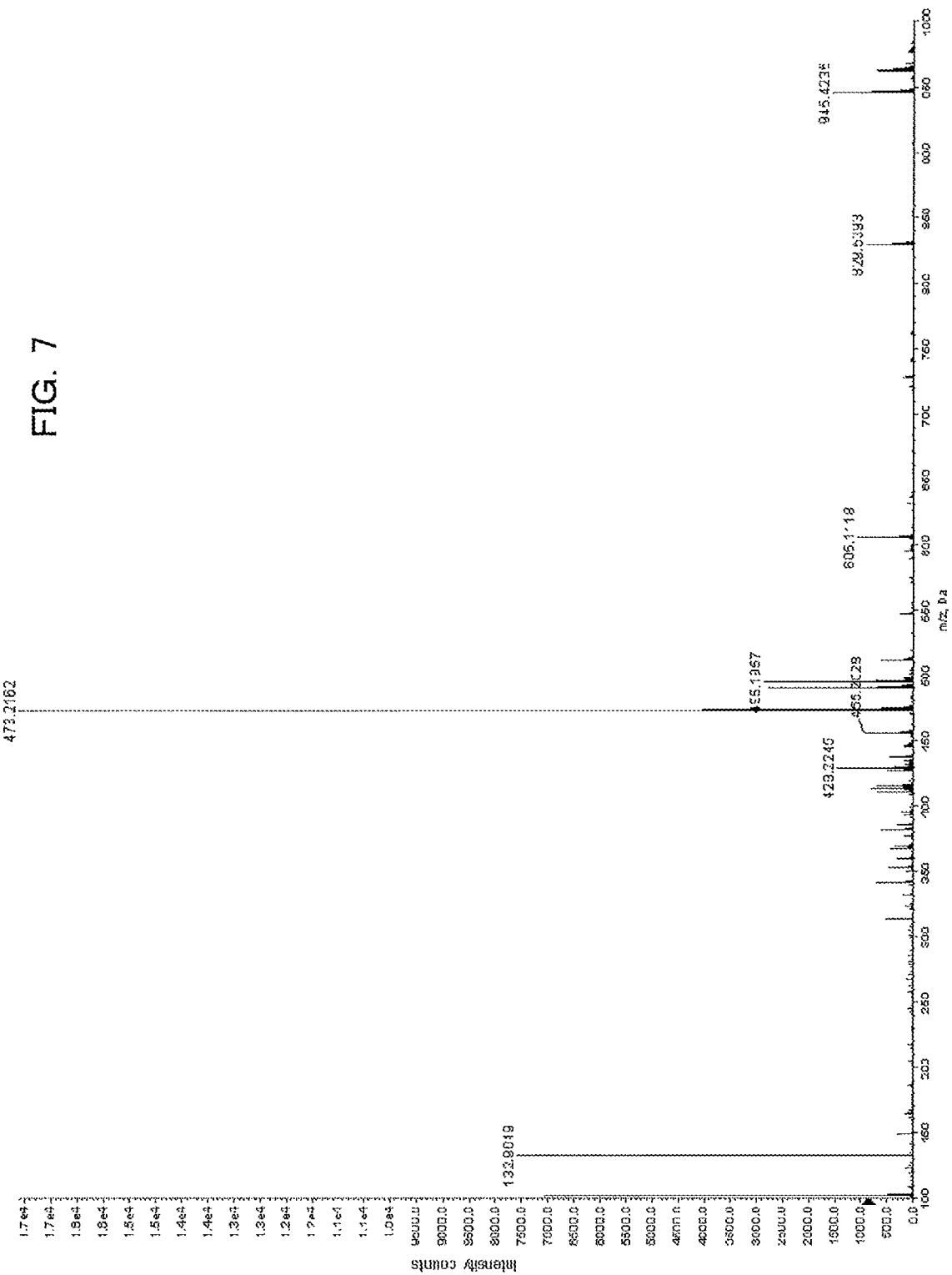
FIG. 7 shows LC-MS analytical data of a limonoid aglycone (i.e., deacetyl nomilin).
Figure 8:
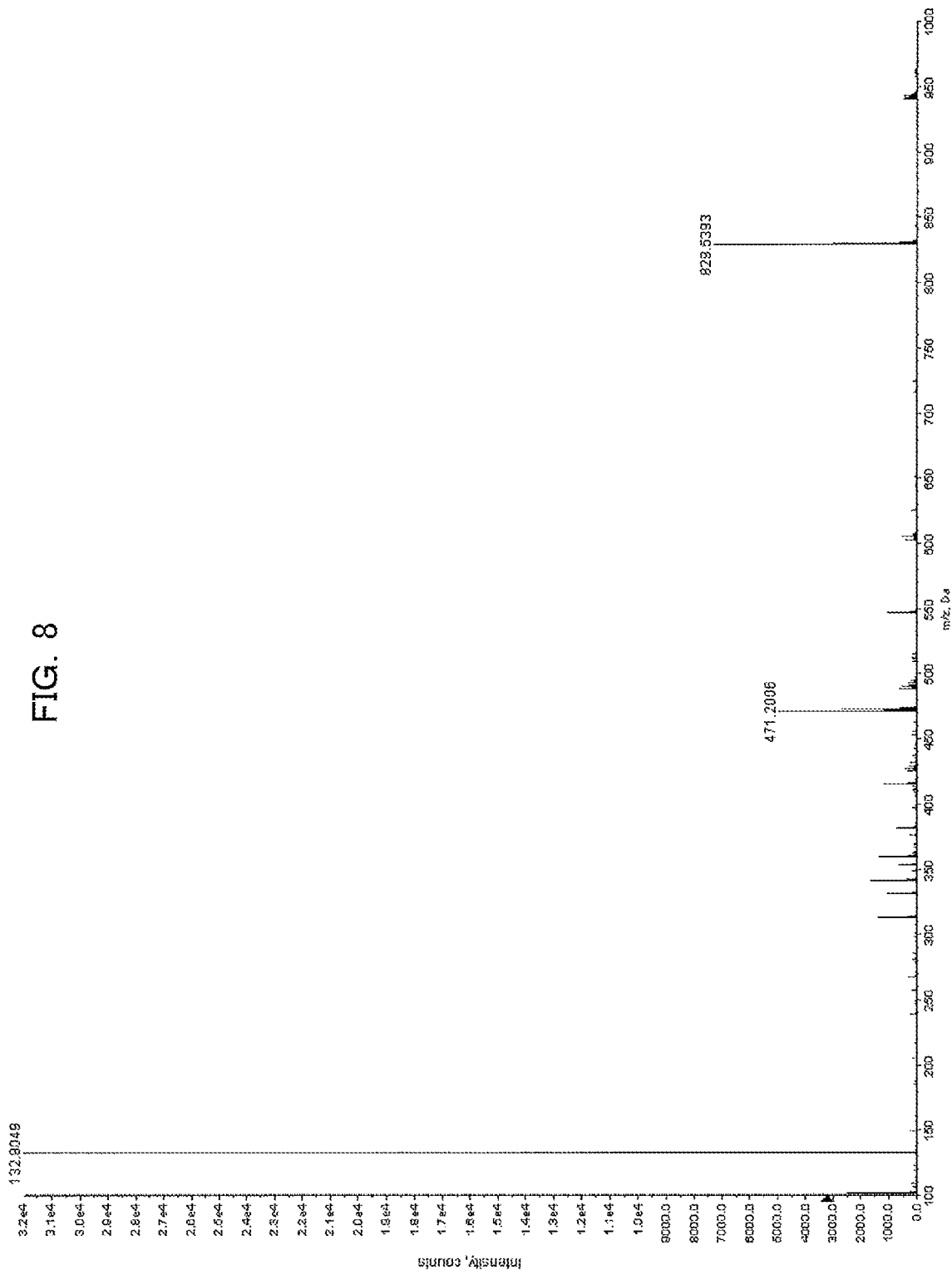
FIG. 8 shows LC-MS analytical data of a limonoid aglycone (i.e., limonin).
Figure 9:
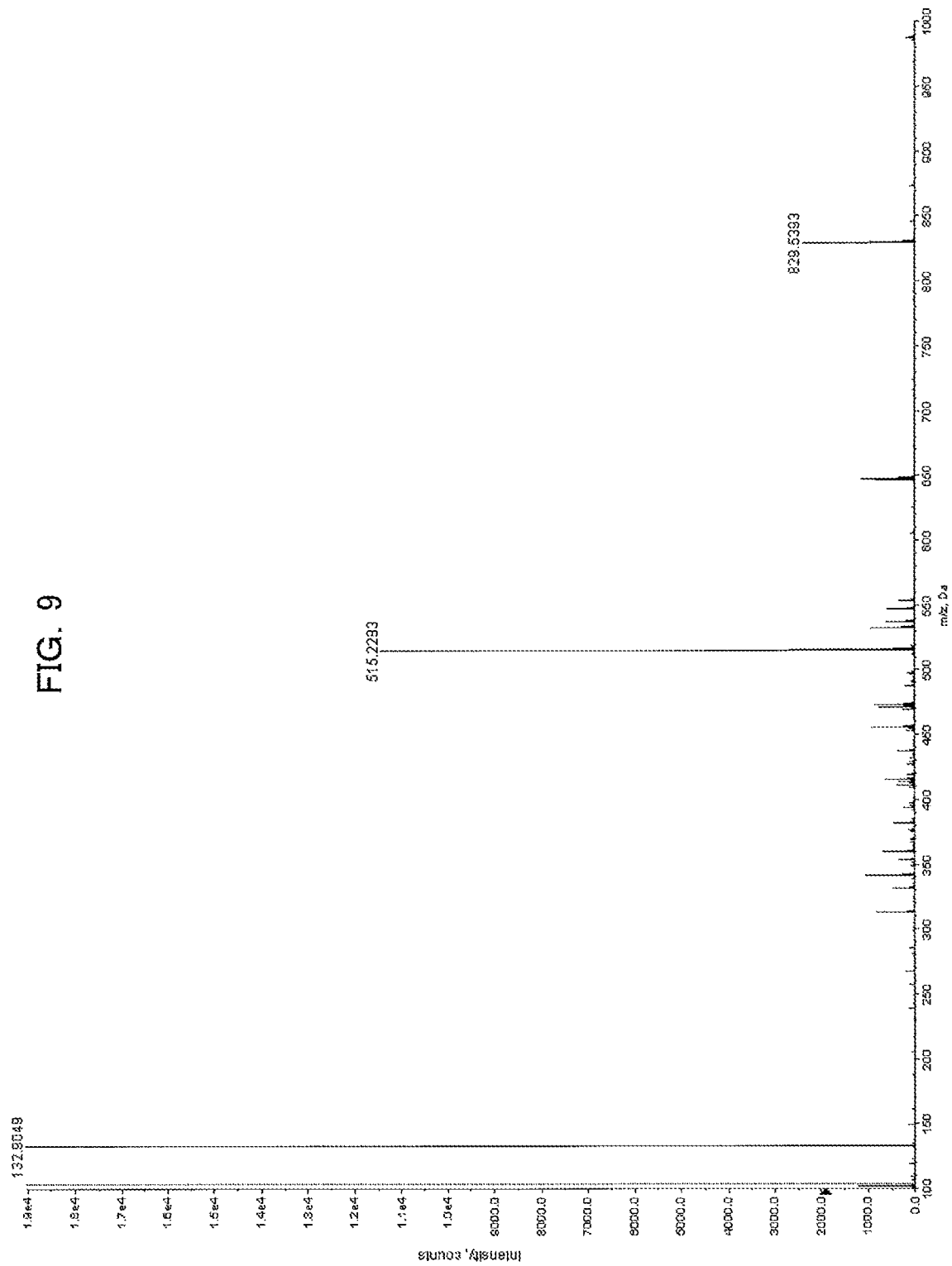
FIG. 9 shows LC-MS analytical data of a limonoid aglycone (i.e., nomilin).
Figure 10:
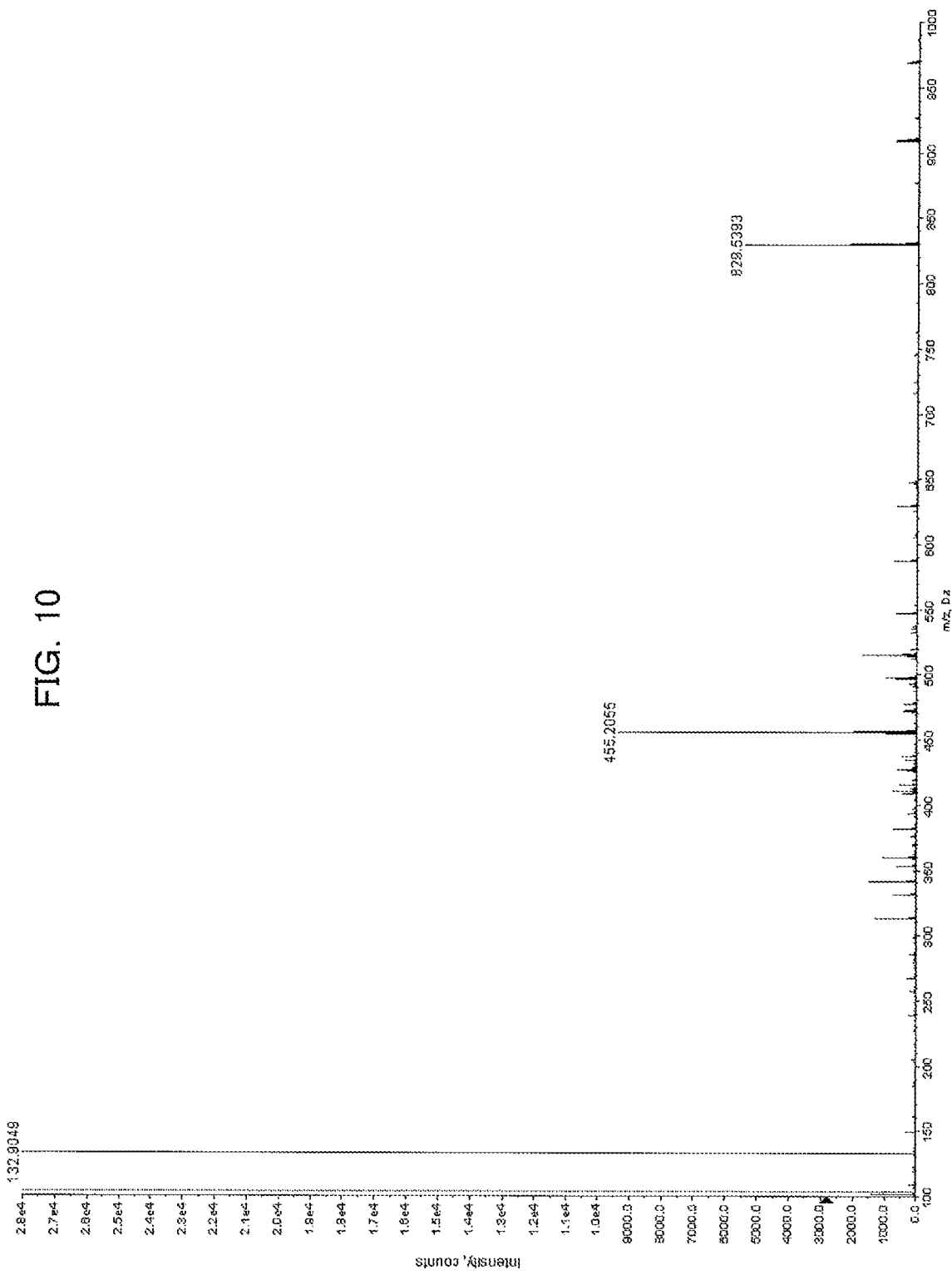
FIG. 10 shows LC-MS analytical data of a limonoid aglycone (i.e., obacunone).

As shown in FIG. 7, the sample shows 473.2162 m/z demonstrating that the limonoid aglycone is deacetyl nomilin (i.e., $[M+H]^+=473.2175$). Further, as shown in FIG. 8, the sample shows 471.2006 m/z demonstrating that the limonoid aglycone is limonin ($[M+H]^+=471.2019$). Moreover, as shown in FIG. 9, the sample shows 515.2283 m/z demonstrating that the limonoid aglycone is nomilin ($[M+H]^+=515.2281$). Furthermore, as shown in FIG. 10, the sample shows 455.2055 m/z demonstrating that the limonoid aglycone is obacunone ($[M+H]^+=455.2070$).

Accordingly, it was confirmed that the limonoid aglycone of the citrus seed (i.e., Yuzu seed) extract-containing composition of the present invention included deacetyl nomilin, limonin, nomilin and obacunone.

Experiment 5

Animal Experiments of KKAy Mice
(Blood-Glucose and HbA1c Levels)

Conditions of the rearing experiment and a method for collecting experimental data were the same as in Experiment 1. However, in the respective groups, 8 mice were used, and water and feed were not fed in free feeding procedure but fed in pair feeding one.

(Composition of Experimental Feed)

AIN-93G containing obacunone (0.035 mass %) was used for the experimental feed.

Here, obacunone used in Experiment 5 was prepared by heat-drying Yuzu seeds at 100° C. for 720 min, and subsequently grinding the dried seeds so that the particle size (diameter) became almost 1 mm or less, performing extraction at an ambient temperature for 10 min with 10-fold volume of 100% ethanol to the Yuzu seeds, and fractionating the resulting extract by silica gel column (daisogel 1002A IR60-40/63A).

Figure 11:
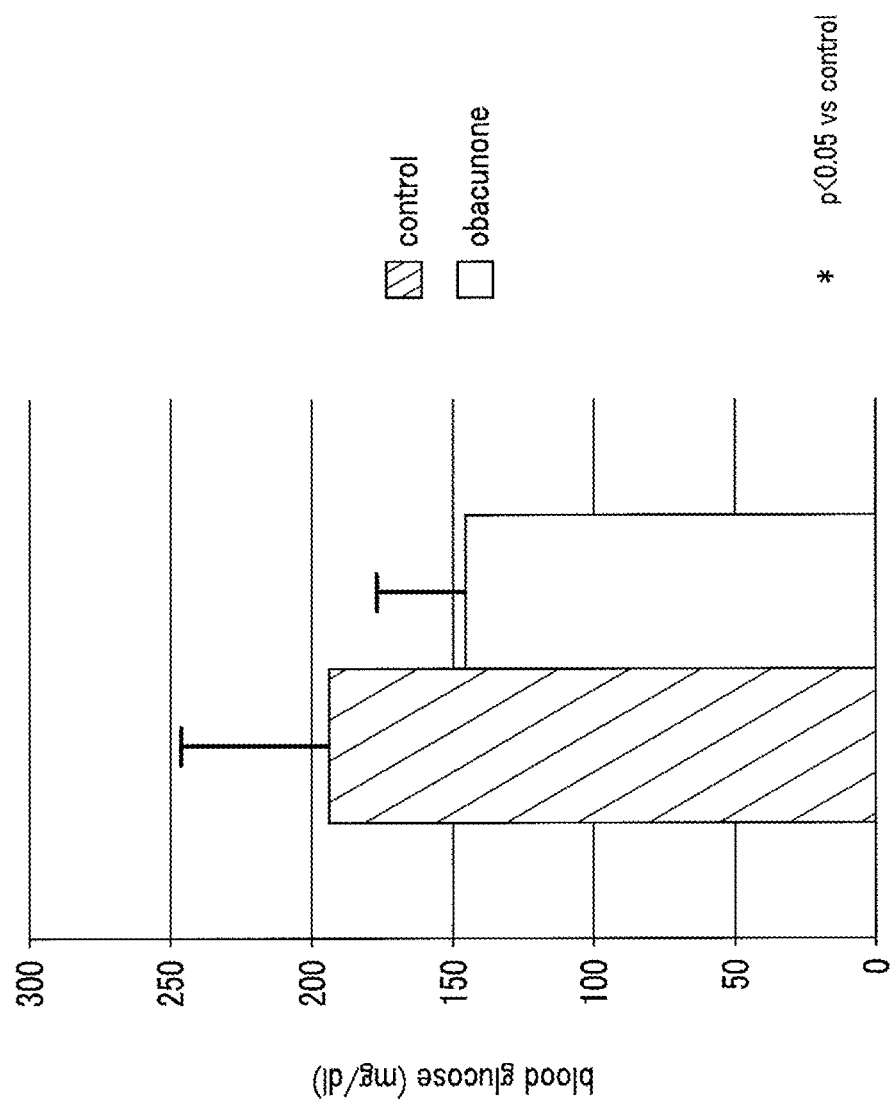
FIG. 11 shows measured data illustrating changes in blood-glucose levels of KKAy mice at the day 28 after starting a rearing experiment.
Figure 12:
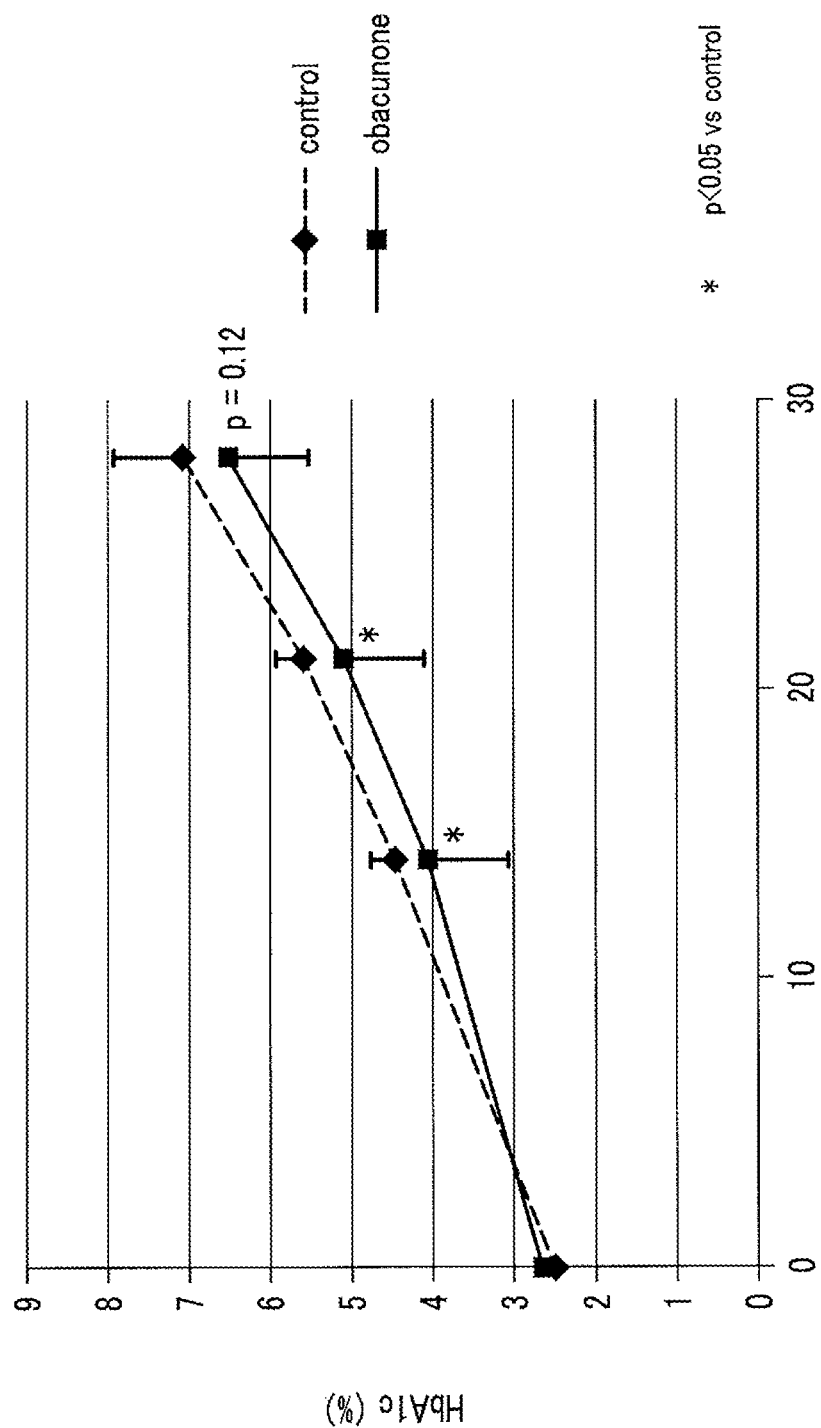
FIG. 12 shows measured data illustrating changes in HbA1c levels of KKAy mice.

FIG. 11 shows blood-glucose levels of the KKAy mice administered with the experimental feed (i.e., at the day 28 after initiation of the rearing experiment). FIG. 12 shows changes in HbA1c levels of the KKAy mice administered with the experimental feed. Here, the ordinate of FIG. 11 represents blood-glucose levels (mg/dl) and the ordinate of FIG. 12 represents HbA1c levels, while the abscissas of FIGS. 11 and 12 represent the number of days (day) having passed after the rearing experiment was initiated.

(Analysis of Experimental Data)

As shown in the data of FIG. 11, the blood-glucose level of the obacunone added group was about 50 mg/dl lower than that of the control group. Further, as shown in the data of FIG. 12, the HbA1c levels of the obacunone added group was lower than those of the control group.

Moreover, it should be noted that the effects shown in FIGS. 11 and 12 were exerted, even when an extremely small quantity (i.e., 0.035 mass %) of obacunone was mixed with the experimental feed. This clearly indicated that an extremely small quantity of obacunone surely exerted the effects of lowering the blood-glucose and HbA1c levels.

Accordingly, it was confirmed that the citrus seed (i.e., Yuzu seed) extract-containing composition including obacunone surely exerted the effects of lowering the blood-glucose and HbA1c levels.

Experiment 6

Dry-Heating Generation of Obacunone and Changes in Generated Quantity Depending on Temperature and Period (Preparation of Experimental Samples)

Yuzu seeds were used as citrus seeds, and subjected to dry-heating. Then, the dried Yuzu seeds were ground so that the particle size (i.e., diameter) became substantially 1 mm or less. Extraction from the ground Yuzu seeds was conducted at an ambient temperature for 10 min using 10-fold volume of 100% ethanol, thereby providing the respective samples.

Here, the term of "dry-heating" in Experiment 6 means a process that the Yuzu seeds were placed in a dry furnace for a predetermined period, at a predetermined temperature.

(Method for Measuring Experimental Samples)

The samples thus provided by the above described method, a nomilin standard and an obacunone standard (ChromaDex, Inc.) were subjected to HPLC analysis following a conventional method, and a nomilin quantity and an obacunone quantity thereof were determined. Based on the measurement values, a "relative quantity of obacunone" and a ratio of "obacunone content/nomilin content" were calculated. The HPLC analysis was performed under the following conditions: Detector 2996-controller 600-autosampler 717 plus system (Waters Co.) and CAPCELL PAK C18 UG120 (150 mm×4.6 mm I.D., Shiseido Co., Ltd.); Elution in Gradient (0 min 85:15→5 min 77:23→25 min 74:26→30 min 60:40→45 min 54:46→51 min), Flow Rate=1 ml/min; Detection Wavelength=210 nm.

Here, the term of a "relative quantity of obacunone" means a relative value. With respect to the samples shown in FIG. 13 and Table 1 (i.e., dry-heating period fixed to 24 hr), a relative quantity of obacunone at 100° C. in the dry-heating is defined to 1.0000. Further, with respect to the samples shown in FIG. 14 and Table 2 (i.e., dry-heating temperature fixed to 150° C.), a relative quantity of obacunone at 30 min in the dry-heating is defined to 1.0000.

Further, the term of an "obacunone content/nomilin content" means a ratio calculated based on a "nomilin content" in a sample calculated by comparing the peak of the nomilin standard to the nomilin peak shown by the sample, and the "obacunone content" in the sample calculated by comparing the peak of the obacunone standard to the obacunone peak shown by the sample.

Figure 13:
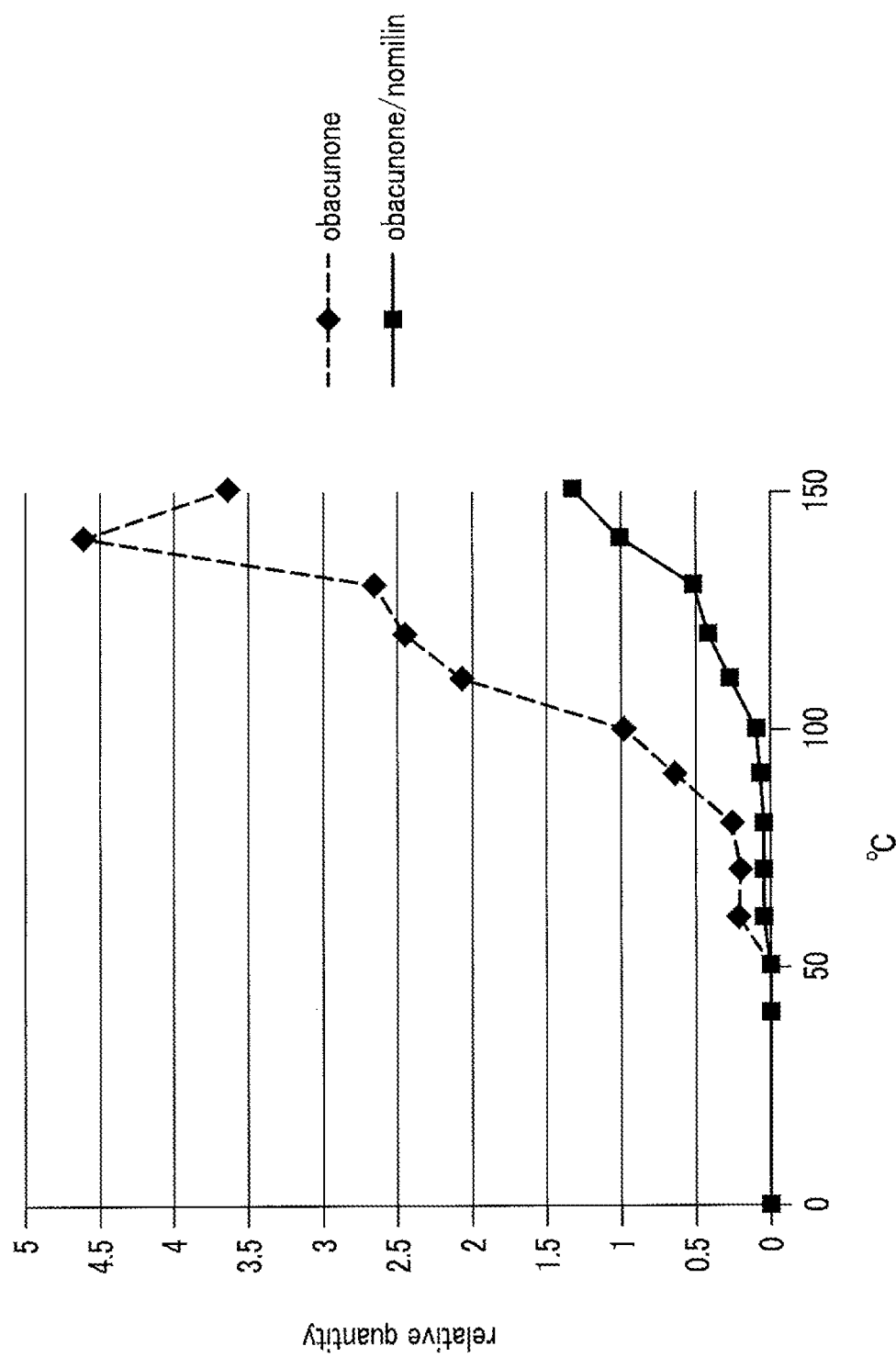
FIG. 13 shows data illustrating how a heating-temperature influences a relative quantity of obacunone as well as a ratio of obacunone content to nomilin content.

Note, FIG. 13 and Table.1 show a "relative quantity of obacunone" and an "obacunone content/nomilin content" measured when a dry-heating period is fixed to 24 hr and a dry-heating temperature is varied. Further, FIG. 14 and Table.2 show a "relative quantity of obacunone" and an "obacunone content/nomilin content" measured when a dry-heating temperature is fixed to 150° C. and a dry-heating period is varied.

Here, in the drawings and tables, the term of "obacunone" represents a "relative quantity of obacunone", and the term of "obacunone/nomilin" represents a ratio of "obacunone content/nomilin content".

TABLE 1

| Dry-Heating Temperature (° C.) | Obacunone/Nomilin (—) | Obacunone (—) |
|---|---|---|
| 0 | 0.0000 | 0.0000 |
| 40 | 0.0000 | 0.0000 |
| 50 | 0.0000 | 0.0000 |
| 60 | 0.0274 | 0.2396 |
| 70 | 0.0232 | 0.2273 |
| 80 | 0.0303 | 0.2718 |
| 90 | 0.0802 | 0.6537 |
| 100 | 0.1150 | 1.0000 |
| 110 | 0.2951 | 2.0789 |
| 120 | 0.4314 | 2.4512 |
| 130 | 0.5257 | 2.6816 |
| 140 | 1.0237 | 4.6148 |
| 150 | 1.3404 | 3.6509 |

TABLE 2

| Dry-Heating Period (min) | Obacunone/Nomilin (—) | Obacunone (—) |
|---|---|---|
| 0 | 0.0000 | 0.0000 |
| 5 | 0.0064 | 0.0255 |
| 10 | 0.0245 | 0.0985 |
| 30 | 0.2228 | 1.0000 |
| 60 | 0.3451 | 1.3467 |
| 180 | 0.6356 | 1.7616 |
| 360 | 0.9342 | 2.3202 |
| 720 | 1.2583 | 2.4326 |
| 1440 | 1.5490 | 2.2784 |
| 2880 | 3.9184 | 2.3585 |
| 4320 | 2.8865 | 2.1438 |

(Analysis of Experimental Data)

As shown in the data of FIG. 13 and Table 1, it was revealed that obacunone was generated when the dry-heating (or heating) temperature was 60° C. or more. Further, the ratio of "obacunone content/nomilin content" became at least 0.020 when the dry-heating (or heating) temperature was at least 60° C.

Figure 14:
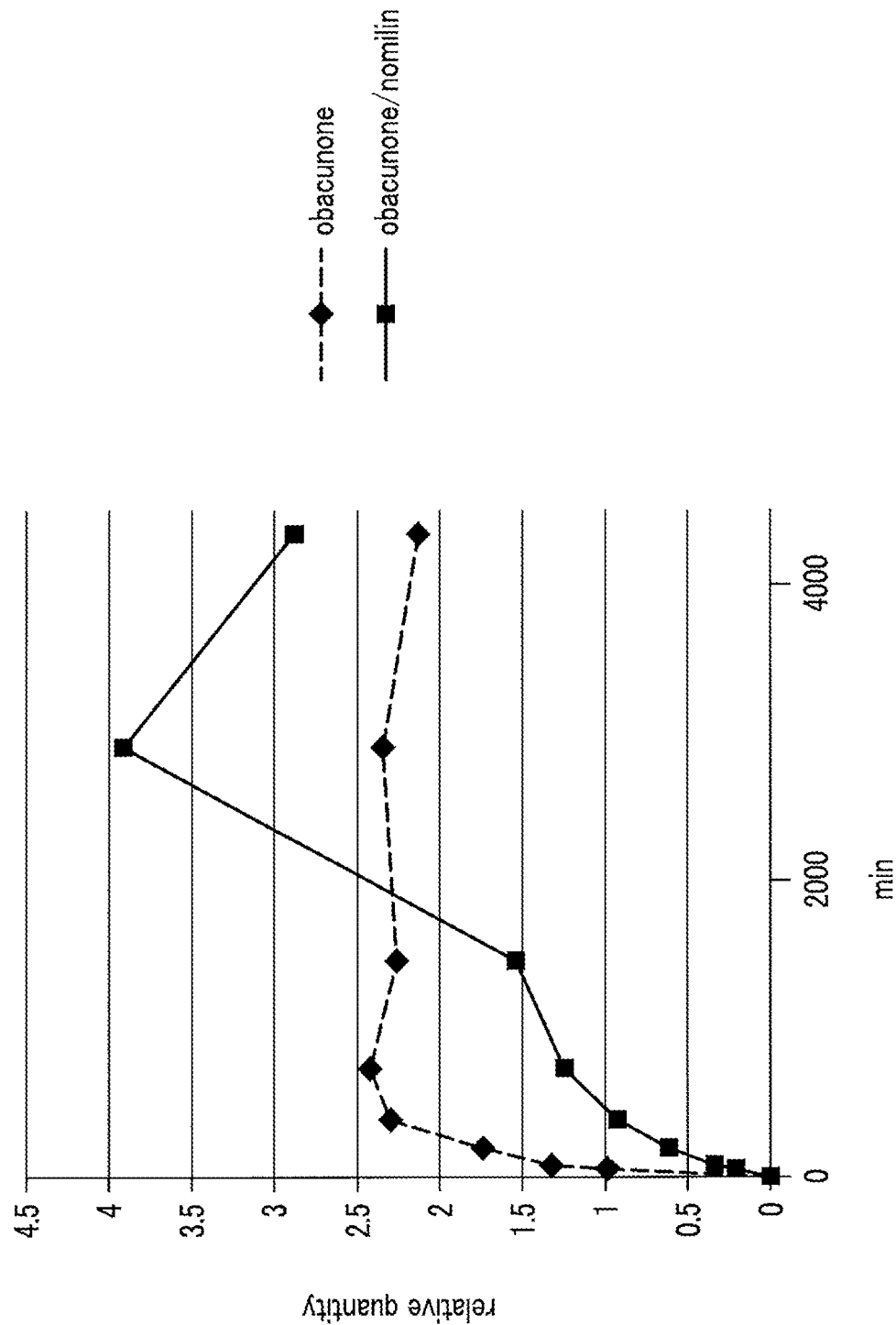
FIG. 14 shows data illustrating how a heating-period influences a relative quantity of obacunone as well as a ratio of obacunone content to nomilin content.

Similarly, as shown in the data of FIG. 14 and Table 2, it was revealed that obacunone was generated when the dry-heating (or heating) period was at least 5 min. Further, the ratio of "obacunone content/nomilin content" became at least 0.020 when the dry-heating (or heating) period was at least 10 min. Herein, when the dry-heating (or heating) period was 1440 min, the nomilin content and the obacunone content in the extraction sample were 133.7 μg/ml and 207.1 μg/ml, respectively. Further, when the dry-heating (or heating) period was 4320 min, the nomilin content and the obacunone content in the extraction sample were 67.5 μg/ml and 194.8 μg/ml, respectively.

As described above, it was confirmed that the method for producing a citrus seed (i.e., Yuzu seed) extraction-containing composition of the present invention produced the composition in which a ratio of "obacunone content/nomilin content" became at least 0.020. In other words, it was confirmed that the method of the present invention definitely produced the composition surely exerting the effects of lowering a blood-glucose level, increasing a skeletal muscle quantity and reducing a body fat, by including the heating step of heating the citrus seeds at 60° C. or more.

Experiment 7

Dry-Heating Generation of Obacunone in Citrus Seeds Other Than Yuzu Seeds (Preparation of Experimental Samples)

"Lemon seeds" and "Grapefruit Seeds" were used as citrus seeds, and the respective seeds were subjected to freeze-drying or dry-heating (i.e., 100° C., 24 hr). After that, the respective seeds were ground so that the particle size (i.e., diameter) became substantially 1 mm or less. Then, extraction was conducted at an ambient temperature for 10 min by using a 10-fold volume of 100% ethanol to the ground Yuzu seeds, thereby to prepare the respective samples.

Herein, the "freeze-drying" in Experiment 7 was conducted by a freeze-dryer RLE-103 (KYOWA VACUUM ENGINEERING CO., LTD.), and drying the frozen samples at −30° C. for 96 hr. Further, the "dry-heating" in Experiment 7 was conducted by placing the respective seeds in a dry furnace for 24 hr at the atmospheric temperature of 100° C.

(Method for Measuring Experimental Samples)

Figure 15:
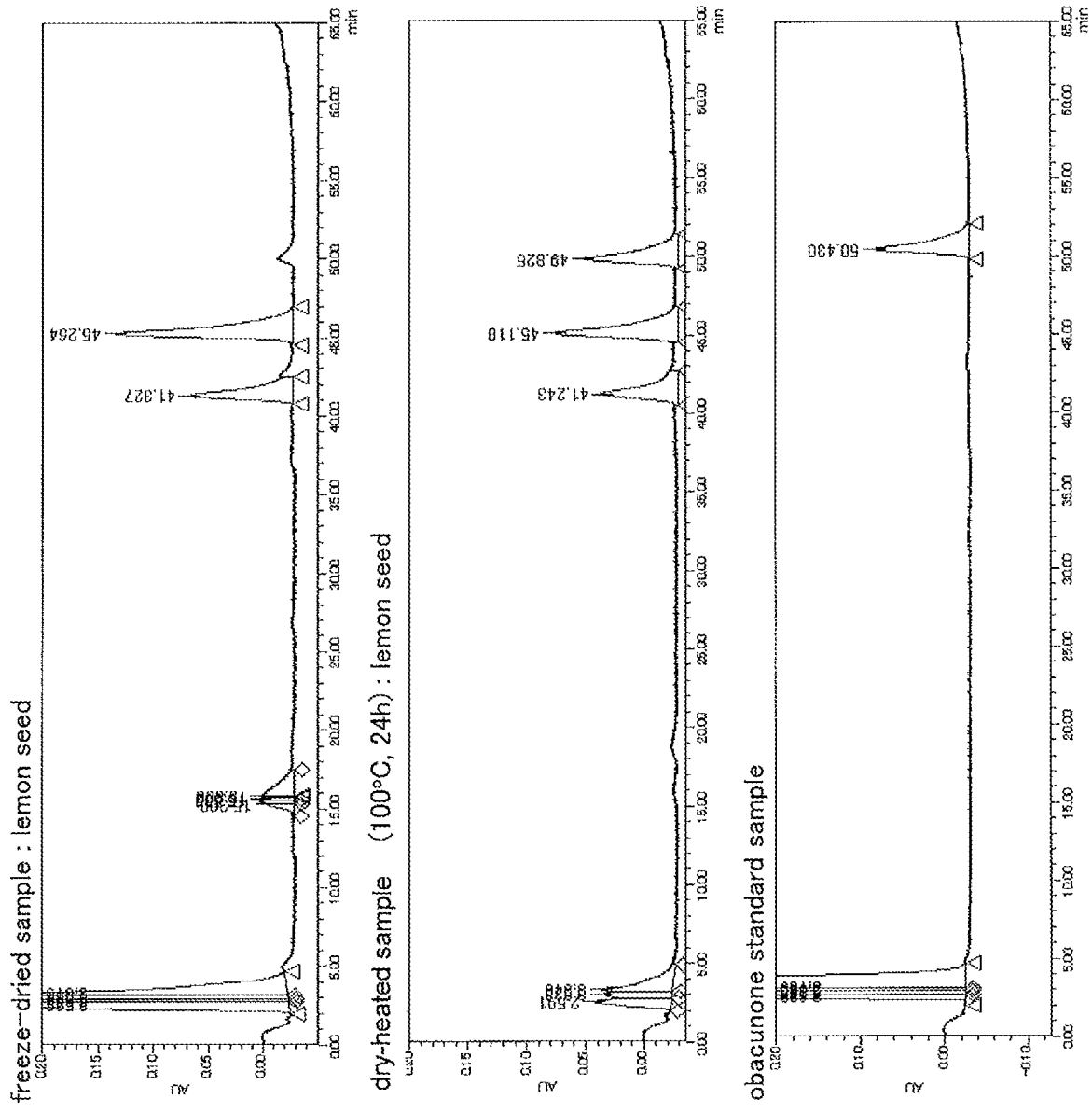
FIG. 15 shows HPLC analytical data of lemon seeds.
Figure 16:
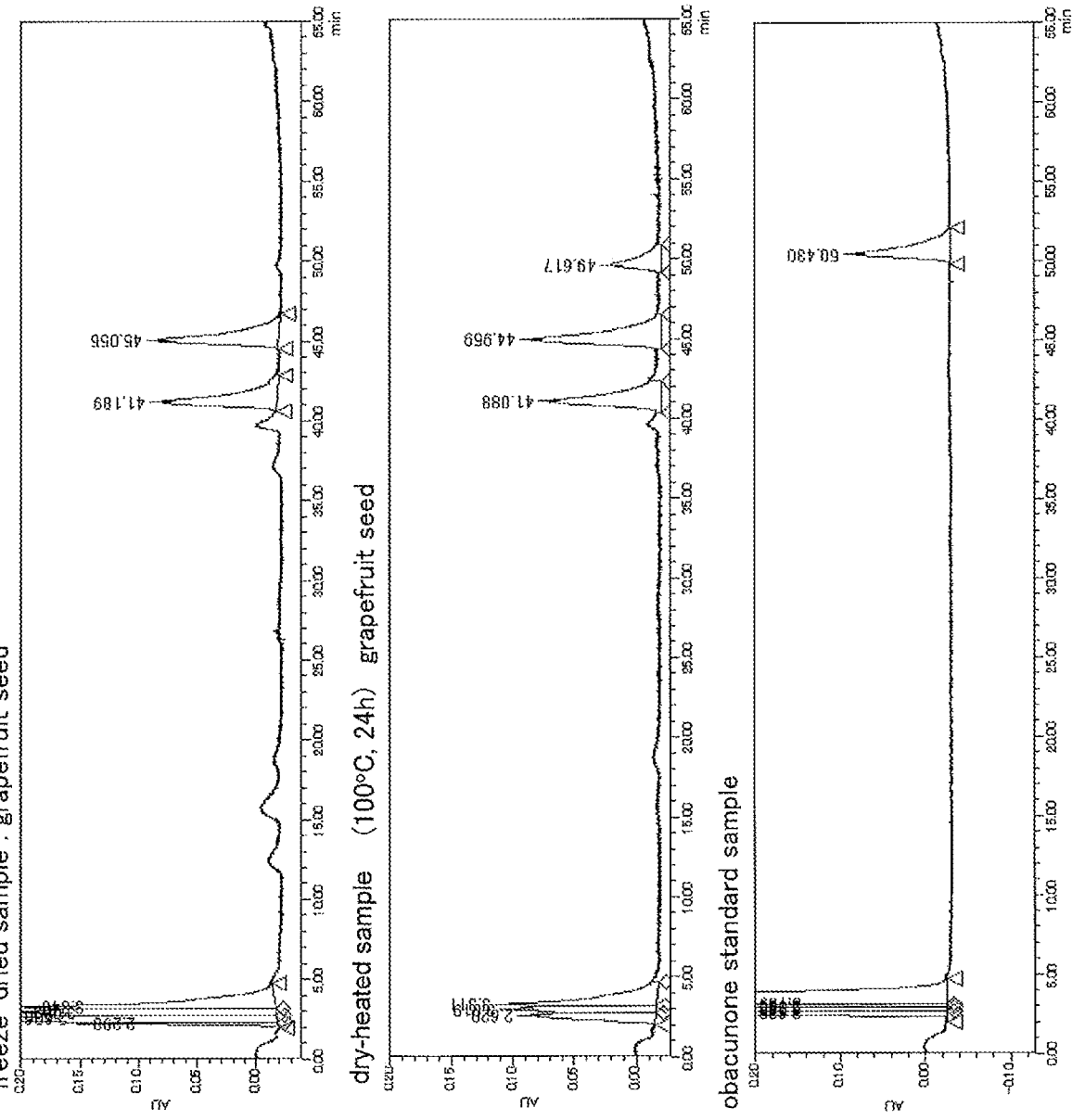
FIG. 16 shows HPLC analytical data of grapefruit seeds.

FIGS. 15 and 16 show the data obtained by the HPLC analysis conducted under the same conditions as in Experiment 6 on the samples prepared by the above described method and an obacunone standard (ChromaDex, Inc.)

Here, the data in FIG. 15 show the absorption spectra of a freeze-dried lemon seed sample, a dry-heated lemon seed sample and an obacunone standard, respectively. Further, the data in FIG. 16 show the absorption spectra of a freeze-dried grapefruit seed sample, a dry-heated grapefruit seed sample and an obacunone standard, respectively.

(Analysis of Experimental Data)

A peak of obacunone was not substantially observed at the retention time shown by the obacunone standard, in both spectra of the freeze-dried seed samples of FIGS. 15 and 16. This result indicated that little obacunone was included in those samples. On the contrary, a large peak of obacunone was observed at the retention time shown by the obacunone standard, in both spectra of the dry-heated seed samples of FIGS. 15 and 16. This result clearly indicated that obacunone was included in those samples.

In other words, it was revealed that obacunone, which was little included in the freeze-dried citrus seed samples, was generated in the dry-heated (or heated) citrus seed samples.

Accordingly, it was confirmed that the method for producing a citrus seed extract-containing composition of the present invention definitely produced a composition containing obacunone via including the heating step of heating the citrus seeds in the method, thereby to surely exert the effects of lowering a blood-glucose level, increasing a skeletal muscle quantity and reducing a body fat.

Hereinbefore, the citrus seed extract-containing composition, the food, the drug, and the method for producing the citrus seed extract-containing composition have been described in detail referring to the embodiments and Examples. However, the scope and spirit of the present invention are not limited to those embodiments and Examples. Needless to say, the scope and spirit of the present invention may be changed or modified based on the descriptions of the attached claims.

EXPLANATION OF REFERENCE NUMBERS

S1 Heating Step
S2 Extraction Step

The invention claimed is:

1. A method for producing a Yuzu seed extract-containing composition comprising the steps of:
   heating Yuzu seeds at 100° C. or more for 720 min or more,
   grinding the heat-dried Yuzu seeds to a diameter of a particle size of 1 mm or less, and
   extracting a Yuzu seed extract from the ground Yuzu seeds in 5 to 60° C. of ethanol;
   wherein the composition is for use in any one selected from the group of lowering a blood-glucose level, increasing a skeleton muscle quantity, and reducing a body fat.

2. The method for producing a citrus seed extract-containing composition of claim 1, wherein a ratio of an obacunone content to a nomilin content in the composition is at least 0.300.

* * * * *